(12) United States Patent
Chen et al.

(10) Patent No.: US 10,856,532 B1
(45) Date of Patent: Dec. 8, 2020

(54) METHOD FOR PRODUCING AN RNAI RESISTANT COLONY OF AN INSECT PEST SPECIES FROM A FIELD-DERIVED POPULATION

(71) Applicant: Monsanto Technology LLC, St. Louis, MO (US)

(72) Inventors: Mao Chen, Chesterfield, MO (US); Thomas L. Clark, Williamsburg, MO (US); Lex E. Flagel, St. Louis, MO (US); Peter D. Jensen, Ballwin, MO (US); Chitvan Khajuria, Ballwin, MO (US); Brian C. McNulty, Chesterfield, MO (US); William Moar, Chesterfield, MO (US); Cara Vazquez, O'Fallon, MO (US)

(73) Assignee: Monsanto Technology LLC, St. Louis, MO (US)

( * ) Notice: Subject to any disclaimer, the term of this patent is extended or adjusted under 35 U.S.C. 154(b) by 27 days.

(21) Appl. No.: 15/909,957

(22) Filed: Mar. 1, 2018

Related U.S. Application Data

(60) Provisional application No. 62/466,939, filed on Mar. 3, 2017.

(51) Int. Cl.
*A01K 67/033* (2006.01)

(52) U.S. Cl.
CPC .................................. *A01K 67/033* (2013.01)

(58) Field of Classification Search
CPC .................................................. A01K 67/033
See application file for complete search history.

(56) References Cited

U.S. PATENT DOCUMENTS

2009/0188005 A1  7/2009  Boukharov et al.
2010/0122381 A1  5/2010  Buehler et al.

OTHER PUBLICATIONS

Bolognesi et al. (2012, PLOS One, vol. 7(10), pp. 1-11). (Year: 2012).*
Baum, J.A., et al., "Control of Coleopteran Insect Pests Through RNA Interference," Nature Biotechnology 25(11):13-22-1326, 2007.
Gong, L., et al., "Silencing of Rieske Iron-Sulfur Protein Using Chemically Synthesised siRNA as a Potential Biopesticide Against Plutella xylostella," Pest Management Science 67:514-520, 2011.
Hu, Y., et al., "High Efficiency Transport of Quantum Dots Into Plant Roots With the Aid of silwet L-77," Plant Physiology and Biochemistry 48(8):703-709, 2010.
Huang, G., et al., "Engineering Broad Root-Knot Resistance in Transgenic Plant by RNAi Silencing of a Conserved and Essential Root-Knot Nematode Parasitism Gene," Proceedings of the National Academy of Sciences of the United States of America 103(39), 14302-14306, 2006.
Li, J., et al., "RNA Interference in Nilaparvata lugens (Homoptera: Delphacidae) Based on dsRNA Ingestion," Pest Management Science 67:852-859, 2011.
Mao, Y.B., et al., "Silencing a Cotton Bollworm P450 Monooxygenase Gene by Plant-Mediated RNAi Impairs Larval Tolerance of Gossypol," Nature Biotechnology 25(11):1307-1313, Nov. 2007.
Moar, W., et al., "Cry3Bb1-Resistant Western Corn Rootworm, *Diabrotica virgifera* (LeConte) Does Not Exhibit Cross Resistance to SvSnf7 dsRNA," PLoS One 12(1):e0169175, 2017.
Pitino, M., et al., "Silencing of Aphid Genes by dsRNA Feeding From Plants," PLoS One 6(10):325709, 2011.
Pridgeon, J.W., et al., "Topically Applied AaelAP1 Double-Stranded RNA Kills Female Adults of Aedes aegypti," Journal of Medical Entomolology 45(3):414-420, 2008.
Sindhu, A.S., et al., "Effective and Specific in Planta RNAi in Cyst Nematodes: Expression Interference of Four Parasitism Genes Reduces Parasitic Success," Journal of Experimental Botany 60(1):315-324, 2008.
Tabashnik, B.E., et al., "Insect Resistance to BT Crops: Lessons From the First Billion Acres," Nature Biotechnology 31(6):510-521, 2013.
Upadhyay, S.K., et al., "RNA Interference for the Control of Whiteflies (*Bemisia tabaci*) by Oral Route," Journal of Biosciences 36(1):153-161, 2011.
Whyard, S., et al., "Ingested Double-Stranded RNAs Can Act as Species-Specific Insecticides," Insect Biochemistry and Molecular Biology 39(11):8224-832, 2009.

* cited by examiner

*Primary Examiner* — Thaian N. Ton
*Assistant Examiner* — David A. Montanari
(74) *Attorney, Agent, or Firm* — Dentons US LLP; Amanda Carmany-Rampey

(57) ABSTRACT

The present invention is directed to a method for producing an RNAi resistant insect pest species colony from an insect pest species isolated from an agricultural field. The invention is also directed to methods for determining the inheritance of resistance to the RNAi and determining the allele frequency of resistance in an agricultural field.

3 Claims, 3 Drawing Sheets

Specification includes a Sequence Listing.

METHOD FOR PRODUCING AN RNAI RESISTANT COLONY OF AN INSECT PEST SPECIES FROM A FIELD-DERIVED POPULATION

REFERENCE TO RELATED APPLICATION

This application claims the benefit of U.S. provisional application No. 62/466,939, filed Mar. 3, 2017, which is herein incorporated by reference in its entirety.

INCORPORATION OF SEQUENCE LISTING

The file named "MONS418US_ST25.txt" containing a computer-readable form of the Sequence Listing was created on Feb. 27, 2018. This file is 3,263 bytes (measured in MS Windows®), is contemporaneously filed by electronic submission (using the United States Patent Office EFS-Web filing system), and is incorporated into this application by reference in its entirety.

FIELD OF THE INVENTION

The invention generally relates to methods of using field-derived colonies of an insect pest species to produce colonies resistant to one or more RNAi (interfering RNA). Further, the disclosed method can be used to determine the inheritance of the resistance, and assess the development of RNAi resistance in an agricultural field of maize plants which express RNAi.

BACKGROUND OF THE INVENTION

Improving crop yield from agriculturally significant plants including, among others, corn, soybean, sugarcane, rice, wheat, vegetables, and cotton, has become increasingly important. In addition to the growing need for agricultural products to feed, clothe and provide energy for a growing human population, climate-related effects and pressure from the growing population to use land other than for agricultural practices are predicted to reduce the amount of arable land available for farming. These factors have led to grim forecasts of food security, particularly in the absence of major improvements in plant biotechnology and agronomic practices. In light of these pressures, environmentally sustainable improvements in technology, agricultural techniques, and pest management are vital tools to expand crop production on the limited amount of arable land available for farming.

Insect pest species, particularly insect pest species within the Coleoptera, Hemiptera, Thysanoptera, and Diptera orders, are considered a major cause of damage to field crops, thereby decreasing crop yields in over infested areas. For example, Coleopteran pests often associated with crop damage and a reduction of yield include, but are not limited to, Western Corn Rootworm (*Diabrotica virgifera virgifera*, WCR), Northern Corn Rootworm (*Diabrotica barberi*, NCR), Mexican Corn Rootworm (*Diabrotica virgifera zeae*, MCR), Banded Cucumber Beetle (*Diabrotica balteata*, BCR), Southern Corn Rootworm (*Diabrotica undecimpunctata howardii*, SCR), Brazilian Corn Rootworm complex (BCR) consisting of *Diabrotica viridula* and *Diabrotica speciosa*), Crucifer Flea Beetle (*Phyllotreta cruciferae*), Striped Flea Beetle (*Phyllotreta striolata*), Western Black Flea Beetle (*Phyllotreta pusilla*), Maize Billbug (*Sphenophorus maidis*), and Southern Corn Billbug (*Sphenophorus callosus*). Hemipteran pests often associated with crop damage and reduced yield, include but are not limited to Stink bugs such as Southern Green Stink Bug (*Nezara viridula*), the Neotropical Brown Stink Bug (*Euschistus heros*), Brown Marmorated Stink Bug (*Halyomorpha halys*), Red-Shouldered Stink Bug (*Thyanta accerra*), the Green Belly Stink Bug (*Dichelops melacanthus*), Tarnished Plant Bug (*Lygus lineolaris*), Western Tarnished Plant Bug (*Lygus hesperus*), Aphids, and Whiteflies. Thysanopteran insect pests associated with crop damage and yield loss include, but are not limited to, Western Flower Thrips (*Frankliniella occidentalis*), Eastern Flower Thrips (*Frankliniella tritici*), Corn Thrips (*Frankliniella williamsi*), Florida Flower Thrips (*Frankliniella bispinosa*), Tobacco Thrips (*Frankliniella fusca*), Tomato Thrips (*Frankliniella schultzei*), and Soybean Thrips (*Sericothrips variabilis*).

Dipteran insect pests that affect agriculture can be insect pest species such as Mosquitoes which can transmit disease to animal livestock, as well as transmit disease to humans. Strategies in which an RNAi is expressed in a transgenic plant can be employed to provide control of Mosquitoes. Mosquito species that transmit disease to humans and animals include, but are not limited to, *Anopheles* spp., Malaria mosquito (*Anopheles quadrimaculatus*), *Anopheles walker*, *Anopheles freeborni*, *Aedes* spp., Yellow Fever Mosquito n(*Aedes aegypti*), Asian Tiger Mosquito (*Aedes albopictus*), *Aedes Canadensis*, *Aedes sollicitans*, *Aedes nigromaculis*, *Culex* spp., *Culex erraticus*, *Culex nigripalpus*, *Culex stigmatosoma*, House Mosquito (*Culex pipiens*, also called *Culex fatigans*), *Culex salinarius*, *Culex tarsalis*, *Culiseta* spp., *Culiseta incidens*, *Culiseta inornata*, *Culiseta melanura*, *Mansonia* spp., *Mansonia titillans*, *Coquillettidia* spp., *Coquillettidia pertubans*, *Psorophora* spp., *Psorophora ciliate*, *Psorophora columbiae* (also called *Psorophora confinnis*), *Psorophora columbiae*, *Psorophora cyanescens*, *Psorophora ferox*, and *Psorophora signipennis*. Dipteran insect pest species that can affect crops include, but are not limited to Midges belonging to the Families Cecidomyiidae such as Hessian fly (*Mayetiola destructor*), Wheat blossom midge (*Sitodiplosis mosellana*), the Asian rice gall midge (*Orseolia oryzae*), African rice gall midge (*Orseolia oryzivora*), Coffee flower midge (*Dasyneura coffeae*), Soybean pod gall midge (*Asphondylia yushimai*); Leaf-Miners belonging to the family Agromyzidae, *Agromyza* spp., *Agromyza abiens*, *Agromyza albipennis*, *Agromyza alnivora*, *Melanagromyza* spp., *Melanagromyza aeneoventris*, *Melanagromyza lappae*, *Melanagromyza albocilia*, *Melanagromyza minimoides*, *Ophiomyia* spp., Asparagus miner (*Ophiomyia simplex*); *Liriomyza* spp., South American leaf miner (*Liriomyza huidobrensis*), American serpentine leaf miner (*Liriomyza trifolii*), Vegetable leaf miner (*Liriomyza sativae*), Tomato leaf miner (*Liriomyza bryoniae*), Serpentine leaf miner (*Lirionyza brassicae*); *Napomyza* spp., *Napomyza lateralis*, *Napomyza bellidis*, *Napomyza carotae*, *Napomyza cichorii*, and *Phytomyza* spp., *Phytomyza ilicis*, *Phytomyza spondylii*, *Phytomyza ilicicola*, *Phytomyza* (*Napomyza*) *gymnostoma*, *Phytomyza horticola*, and *Phytomyza aquilegivora*; and Root Maggots belonging to the family Anthomyiidae, *Delia* spp., Onion fly (*Delia antiqua*), Wheat bulb fly (*Delia coarctata*), Turnip root fly (*Delia floralis*), Seed corn maggot (*Delia platura*), and Cabbage root fly (*Delia radicum*).

Historically, the intensive application of synthetic chemical insecticides was relied upon as the pest control agent in agriculture. Concerns for the environment and human health, in addition to emerging resistance issues, stimulated the research and development of biological pesticides. This research effort led to the progressive discovery and use of various entomopathogenic microbial species, including bacteria.

The biological control paradigm shifted when the potential of entomopathogenic bacteria, especially bacteria belonging to the genus *Bacillus*, was discovered and developed as a biological pest control agent. Strains of the bacterium *Bacillus thuringiensis* (Bt) have been used as a source for pesticidal proteins since it was discovered that Bt strains show a high toxicity against specific insect pest species. Bt strains are known to produce delta-endotoxins that are localized within parasporal crystalline inclusion bodies at the onset of sporulation and during the stationary growth phase (e.g., Cry proteins), and are also known to produce secreted insecticidal protein. Upon ingestion by a susceptible insect pest, delta-endotoxins as well as secreted toxins exert their effects at the surface of the midgut epithelium, disrupting the cell membrane, leading to cell disruption and death. Genes encoding insecticidal proteins have also been identified in bacterial species other than Bt, including other *Bacillus* and a diversity of additional bacterial species, such as *Brevibacillus laterosporus, Lysinibacillus sphaericus* ("Ls" formerly known as *Bacillus sphaericus*) and *Paenibacillus popilliae*.

RNA interference (RNAi, RNA- or dsRNA-mediated gene suppression, and these terms are intended to be used interchangeably) is another approach used for pest control. In invertebrates RNAi-based gene suppression was first demonstrated in nematodes (Fire et al., (1998) *Nature*, 391:806-811; Timmons & Fire (1998) *Nature*, 395:854). Subsequently, RNAi-based suppression of invertebrate genes using recombinant nucleic acid techniques has been reported in a number of species, including agriculturally or economically important pests from various insect and nematode taxa, such as: root-knot nematodes (*Meloidogyne* spp.), see Huang et al. (2006) *Proc. Natl. Acad. Sci. USA*, 103: 14302-14306, doi:10.1073/pnas.0604698103); cotton bollworm (*Helicoverpa armigera*), see Mao et al. (2007) *Nature Biotechnol.*, 25:1307-1313, doi:10.1038/nbt1352; Western corn rootworm (*Diabrotica virgifera* LeConte), see Baum et al. (2007) *Nature Biotechnol.*, 25:1322-1326, doi:10.1038/nbt1359; sugar beet cyst nematode (*Heterodera schachtii*), see Sindhu et al. (2008) *J. Exp. Botany*, 60:315-324, doi: 10.1093/jxb/ern289; mosquito (*Aedes aegypti*), see Pridgeon et al. (2008) *J. Med. Entomol.*, 45:414-420, doi:full/10.1603/0022-2585%282008%2945%5B414%3ATAADRK%5D2.0.CO %3B2 fruit flies (*Drosophila melanogaster*), flour beetles (*Tribolium castaneum*), pea aphids (*Acyrthosiphon pisum*), and tobacco hornworms (*Manduca sexta*), see Whyard et al. (2009) *Insect Biochem. Mol. Biol.*, 39:824-832, doi:10.1016/j.ibmb.2009.09.00; diamondback moth (*Plutella xylostella*), see Gong et al. (2011) *Pest Manag. Sci.*, 67: 514-520, doi:10.1002/ps.2086; green peach aphid (*Myzus persicae*), see Pitino et al. (2011) PLoS ONE, 6:e25709, doi:10.1371/journal.pone.0025709; brown planthopper (*Nilaparvata lugens*), see Li et al. (2011) *Pest Manag. Sci.*, 67:852-859, doi:10.1002/ps.2124; and whitefly (*Bemisia tabaci*), see Upadhyay et al. (2011) *J. Biosci.*, 36:153-161, doi:10.1007/s12038-011-9009-1.

A method for control of CRW using RNA-mediated gene suppression has been developed in which transgenic maize plants such as corn, express a dsRNA that suppresses an mRNA encoding an essential protein, resulting in the death of the CRW consuming any such dsRNA. The dsRNA targeted for suppression encodes a DvSnf7 protein, and the dsRNA and the RNAi approach for controlling corn rootworms is ubiquitous in the *Diabrotica* species referred to as corn rootworms, i.e., including being effective against Western Corn Rootworm (*Diabrotica virgifera virgifera*, WCR) and Northern Corn Rootworm (*Diabrotica barberi*, NCR). Ingestion of the dsRNA either through an artificial insect diet or corn plant roots expressing the dsRNA results in mortality and/or stunting of the CRW. Such a method has proven successful in controlling CRW and provides an additional mode of action in controlling CRW species infestation of corn in addition to that of traditional *Bacillus thuringiensis*-derived toxins (Baum et al. (2007) *Nature Biotechnol.*, 25:1322-1326, doi:10.1038/nbt1359).

Three *Bacillus thuringiensis*-derived toxins have been used in transgenic maize for management of Western Corn Rootworm: Cry3Bb1, mCry3A, and Cry34/35Ab1. In 2009, farmers in Iowa observed severe injury to Cry3Bb1 maize by larval Western Corn Rootworm in the field, and subsequent laboratory assays revealed that this injury was associated with Cry3Bb1 resistance. Injury to Cry3Bb1 maize in the field has persisted through 2015 and expanded to include maize encoding mCry3A and Cry34/35Ab1 proteins. Analysis of Western Corn Rootworm collected in 2011 revealed that (i) severe injury to Cry3Bb1 maize and mCry3A maize in the field was associated with resistance, and (ii) cross-resistance between Cry3Bb1 and mCry3A was present (Gassmann et al. (2013) Current Issue, 111(14): 5141-5146, doi: 10.1073/pnas.1317179111).

While resistance to dsRNA has not been reported in field studies in which dsRNA expressing plants are used to control an insect pest species, there is always the potential for resistance to develop to the dsRNA under the right selection pressures. As the dsRNA technology becomes more widely adapted in the coming years, greater exposure of populations of insect pest species to a dsRNA may increase the probability of colonies of specific insect pest species developing resistance to the dsRNA. Therefore, it would be of great advantage to develop under laboratory conditions a dsRNA resistant colony of an insect species in order to better understand the likelihood of resistance development, the selective pressures that would permit such resistance to occur, and the mechanism of resistance.

Thus, the inventors disclose herein, a method for producing an RNAi resistant colony of and insect pest species. The RNAi resistant colony is produced using colonies of an insect pest species isolated from agricultural fields comprising plants which express an RNAi and agricultural fields that comprise plants that do not express the RNAi. The RNAi resistant colony or colonies can be used through breeding experiments to assess the inheritance of the RNAi resistance trait. In addition, the RNAi resistant colony can be used to assess the frequency of the resistance allele in a field, to map the resistance allele or alleles on the chromosome of an insect pest species, and to develop compositions and methods for mediating or overcoming the resistance mechanism. Knowledge of the gene or genes involved in conferring such resistance can lead to new strategies of insect management and resistance management.

SUMMARY OF THE INVENTION

Disclosed herein is a method for producing an RNAi resistant colony of an insect pest species. The resultant RNAi resistant colony can be used in breeding experiments with a dsRNA susceptible colony to map the locus or loci responsible for resistance to the RNAi. The RNAi resistant insect pest species colony can also be used to determine the inheritance, allele frequency in a field, and to discover the mechanism for resistance to an RNAi. In addition, the RNAi resistant colony can be used to understand the potential or probability for RNAi resistance to develop in an agricultural field comprising plants expressing an RNAi.

In one embodiment, disclosed in this application is a method for producing a race of an insect pest species exhibiting decreased susceptibility to dsRNA mediated gene suppression, the method comprising: (a) collecting an insect pest species from an agricultural field site comprising plants that express a dsRNA targeting an essential gene in said pest for suppression; (b) collecting an insect pest species from an agricultural field site comprising plants devoid of said dsRNA; (c) crossing male insects obtained from each of steps a. and b. separately with females of said insect pest species that exhibit susceptibility to the dsRNA and obtaining F1 progeny from each such cross; (d) feeding said F1 progeny on a diet lacking the dsRNA and obtaining F2 and successive generations of progeny; (e) feeding F2 and successive generations of progeny derived from insects of step a. on a diet comprising dsRNA sufficient to inhibit said insect pest species members that are susceptible to dsRNA mediated gene suppression; (f) selecting survivors from step e. as individuals exhibiting decreased susceptibility to dsRNA mediated gene suppression; (g) feeding F2 and successive generations of progeny derived from insects of step b. on a diet devoid of dsRNA; and (h) selecting insects susceptible to the RNAi from the progeny of g. that, when fed on a diet comprising an ordinarily pest inhibitory effective amount of the dsRNA, or on plants expressing an ordinarily pest inhibitory effective amount of the dsRNA, results in mortality of the insect pest species, wherein the pest inhibitory effective amount of the dsRNA is sufficient to kill a susceptible insect pest species.

In another embodiment, the method further comprises: (i) mating the dsRNA resistant insect pest species derived from step (f) with individuals susceptible to the dsRNA; wherein progeny are produced; (j) feeding said progeny with a diet comprising an amount of said dsRNA that is ordinarily a pest inhibitory effective amount to a susceptible individual; (k) analyzing the mortality rates of said progeny; and (1) selecting individuals that are least impacted by said dsRNA. Further, the progeny of (i) can be backcrossed with an insect pest species colony exhibiting resistance to said dsRNA.

In another embodiment of the invention is an isolated and purified colony of insect pest species resistant to the RNAi produced by the method comprising: (i) mating the dsRNA resistant insect pest species derived from step (f) with individuals susceptible to the dsRNA; wherein progeny are produced; (j) feeding said progeny with a diet comprising an amount of said dsRNA that is ordinarily a pest inhibitory effective amount to a susceptible individual; (k) analyzing the mortality rates of said progeny; and (1) selecting individuals that are least impacted by said dsRNA.

The method can be used to determine the inheritance of resistance to the dsRNA in a field-derived colony of an insect pest species that comprises field-evolved resistance to the RNAi.

In another embodiment of the invention, the females used in the first cross (step c) to produce a race of an insect pest species exhibiting decreased susceptibility to dsRNA mediated gene suppression are non-diapausing.

In yet another embodiment of the invention, the dsRNA is an miRNA, siRNA, or a dsRNA. In a further embodiment of the invention, the dsRNA targets for suppression the endogenous corn rootworm gene DvSnf7.

Also contemplated in this application is a method for determining the frequency of resistance alleles for resistance to at least one dsRNA in populations of an insect pest species in which resistance to the dsRNA has not evolved, the method comprising: (a) providing an insect pest species collected from a field; (b) mating virgin adults of said insect pest species from the collected insect pest species with virgin adults from the insect pest species resistant to the dsRNA from a field-derived colony, whereby progeny larvae are produced, and wherein the resistant insect pest species comprise resistance to the dsRNA; (c) allowing the larvae to feed on a diet comprising a pest inhibitory effective amount of the dsRNA, or upon plants expressing a pest inhibitory effective amount of the dsRNA, wherein the pest inhibitory effective amount of the dsRNA is sufficient to kill the insect pest species susceptible to the dsRNA but does not kill the insect pest species resistant to the dsRNA; and (d) determining mortality of the larvae of step (c). Further, the at least one dsRNA is a miRNA, siRNA, or dsRNA. Yet further, the at least one dsRNA is a dsRNA that targets for suppression the corn rootworm gene DvSnf7.

The insect pest species used in the method for producing a race of an insect pest species exhibiting decreased susceptibility to dsRNA mediated gene suppression is selected from the group consisting of Coleoptera, Hemiptera, Diptera, and Thysanoptera.

The Coleoptera can be selected from the group consisting of *Agriotes* spp., *Anthonomus* spp., *Atomaria linearis, Cerotoma* spp., *Chaetocnema tibialis, Chrysomelidae, Cosmopolites* spp., *Curculionidae, Curculio* spp., *Cylas* spp. *Dermestes* spp., *Diabrotica* spp., *Epilachna* spp., *Eremnus* spp., *Lissorhoptrus* spp., *Melolontha* spp., *Orycaephilus* spp., *Otiorhynchus* spp., *Phyllophaga* spp., *Phlyctinus* spp., *Popillia* spp., Japanese beetle (*Popillia japonica*), *Psylliodes* spp., *Rhizopertha* spp., *Scarabeidae, Sitophilus* spp., *Sitotroga* spp., *Tenebrio* spp., *Tribolium* spp. and *Trogoderma* spp, *Leptinotarsa decemlineata, Diabrotica balteata, Diabrotica barberi, Diabrotica beniensis, Diabrotica cristata, Diabrotica curvipustulata, Diabrotica dissimilis, Diabrotica elegantual, Diabrotica emorsitans, Diabrotica graminea, hispanolae, lemniscata, Diabrotica linsleyi, Diabrotica longicornis, Diabrotica milleri, Diabrotica nummularis, Diabrotica occlusa, Diabrotica porracea, Diabrotica scutellata, Diabrotica speciosa, Diabrotica tibialis, Diabrotica trifasciata, Diabrotica undecimpunctata, Diabrotica virgifera, Diabrotica viridula, Diabrotica virgifera virgifera, Diabrotica barberi, Diabrotica virgifera zeae, Diabrotica balteata, Diabrotica undecimpunctata howardii, Diabrotica viridula, Diabrotica speciosa, Phyllotreta cruciferae, Phyllotreta striolata, Phyllotreta pusilla, Sphenophorus maidis, Sphenophorus callosus, Oulema melanoplus, Colaspis brunei, Carpophilus dimidiatus, Carpophilus lugubris, Glischrochilus quadrisignatus, Stenolophus lecontei, Clivina impressifrons, Myochrous denticollis, Euetheola humiis rugiceps, Cyclocephala* spp. and *Phyllophaga* spp, *Aeolus* spp. *Conderus* spp. *Limonius, Hemicrepidius* spp. *Agriotes* spp., and *Melanotus* spp.

The Hemiptera can be selected from the group consisting of *Chinavia hilaris, Chinavia marginata, Chinavia pensylvanica, Chlorochroa granulose, Chlorochroa kanei, Chlorochroa ligata, Chlorochroa lineate, Chlorochroa opuntiae, Chlorochroa persimilis, Chlorochroa rossiana, Chlorochroa sayi, Chlorochroa uhleri, Chlorochroa belfragii, Chlorochroa faceta, Chlorochroa osborni, Chlorochroa saucia, Chlorochroa senilis, Nezara viridula, Edessa meditabunda, Edessa bifida*, and *Edessa florida, Euschistus heros, Euschistus acuminatus, Euschistus biformis, Euschistus conspersus, Euschistus crenator, Euschistus egglestoni, Euschistus ictericus, Euschistus inflatus, Euschistus latimarginatus, Euschistus obscures, Euschistus politus, Euschistus* quadrator, Euschistus sevus, Euschistus strenuous, Euschistus tristigmus, Euschistus variolarius, Halyomorpha halys, Thyanta accerra, Thyanta calceata, Thyanta custator, Thyanta pallidovirens, Thyanta perditor, Thyanta maculate, Thyanta pseudocasta, Dichelops melacanthus, Dichelops avilapiresi, Dichelops bicolor, Dichelops dimidatus, Dichelops furcatus, Dichelops furcifrons, Dichelops lobatus, Dichelops miriamae, Dichelops nigrum, Dichelops peruanus, Dichelops phoenix, and Dichelops saltensis, Piezodorus guildinni, Piezodorus lituratus, Megacopta cribraria, Blissus leucopterus leucopterus, Lygus lineolaris, Lygus hesperus, Aphis fabae, Brevicoryne brassicae, Myzus persicae, Aphis gossypii, Macrosiphum euphorbiae, Aphis pomi, Brachycaudus helichrysi, Hyalopterus pruni, Dysaphis plantaginea, Eriosoma lanigerum, Prociphilus spp., Sarucallis kahawaluokalani, Cinara spp., Shivaphis celti, Aphis nerii, Macrosiphum rosae, Illinoia liriodendra, Aonidiella aurantii, Furchadaspis zamiae, Unaspis euonymi, Hemiberlesia rapax, Hemiberlesia lataniae, Carulaspis minima, Melanaspis obscura, Aspidiotus nerii, Parlatoria oleae, Lepidosaphes ulmi, Lepidosaphes beckii, Quadraspidiotus perniciosus, Quadraspidiotus juglansregiae, Siphoninus phillyreae, Trialeurodes vaporariorum, Trialeurodes abutilonea, Aleyrodes spiraeoides, Dialeurodes citri, Tetraleurodes mori, Aleuroplatus coronate, Bemisia tabaci, Aleurodicus dugesii, and Aleurothrixus floccosus.

The Diptera Anopheles spp., Anopheles quadrimaculatus, Anopheles walker, Anopheles freeborni, Aedes spp., Aedes aegypti, Aedes albopictus, Aedes Canadensis, Aedes sollicitans, Aedes nigromaculis, Culex spp., Culex erraticus, Culex nigripalpus, Culex stigmatosoma, Culex pipiens, Culex fatigans, Culex salinarius, Culex tarsalis, Culiseta spp., Culiseta incidens, Culiseta inornata, Culiseta melanura, Mansonia spp., Mansonia titillans, Coquillettidia spp., Coquillettidia pertubans, Psorophora spp., Psorophora ciliate, Psorophora columbiae, Psorophora confinnis, Psorophora columbiae, Psorophora cyanescens, Psorophora ferox, and Psorophora signipennis, Mayetiola destructor, Sitodiplosis mosellana, Orseolia oryzae, Orseolia oryzivora, Dasyneura coffeae, Asphondylia yushimai, Thecodiplosis japonensis, Contarinia lentis, Contarinia medicaginis, Dasineura ignorata, Obolodiplosis robiniae, Contarinia nasturtii, Dasineura brassicae, Contarinia pyrivora, Resseliella theobaldi, Horidiplosis ficifolii, Rhopalomyia solidaginis, Porrcondylini spp., Lestremia spp., Lestodiplosis spp., Acaroletes spp., Aphidoletes spp., Lestodiplosis spp., Acaroletes spp., Aphidoletes spp., and Arthrocnodax spp., Agromyza spp., Agromyza abiens, Agromyza albipennis, Agromyza alnivora, Agromyza ambigua, Agromyza apfelbecki, Agromyza cinerascens, Agromyza drepanura, Agromyza frontella, Agromyza intermittens, Agromyza luteitarsis, Agromyza megalopsis, Agromyza nana, Agromyza nigrella, Agromyza nigrociliata, Agromyza oryzae, Agromyza parvicornis, Agromyza rondensis, Agromyza yanonis; Melanagromyza spp., Melanagromyza aeneoventris, Melanagromyza lappae, Melanagromyza albocilia, Melanagromyza minimoides, Melanagromyza obtuse, Melanagromyza sojae, Melanagromyza Hendel, Melanagromyza splendid, Melanagromyza ricini, Melanagromyza obtuse, Melanagromyza aenea; Ophiomyia spp., Opiioryia sinplex, Lirionyza spp., Liriomyza huidobrensis, Liriomyza trifolii, Liriomyza sativae, Liriomyza bryoniae, Lirionyza brassicae, Napomyza spp., Napomyza lateralis, Napomyza bellidis, Napomyza carotae, Napomyza cichorii, Phytomyza spp., Phytomyza ilicis, Phytomyza spondylii, Phytomyza ilicicola, Phytomyza (Napomyza) gymnostoma, Phytomyza horticola, Phytomyza aquilegivora, Delia spp., Delia antique, Delia coarctata, Delia floralis), Delia platura), Delia radicum.

The Thysanoptera can be selected from the group consisting of Frankliniella occidentalis, Frankliniella tritici, Frankliniella williamsi, Frankliniella bispinosa, Frankliniella fusca, Frankliniella schultzei, Sericothrips variabilis, Gynaikothrips ficorum, Gynaikothrips uzeli, Holopothrips tabebuia, Thrips calcaratus, Thrips palmi, Thrips simplex, Thrips tabaci, Scirtothrips citri, Scirtothrips dorsalis, Scirtothrips perseae, Chaetanaphothrips orchidii, Echinothrips americanus, Taeniothrips inconsequens, Caliothrips fasciatus, Heliothrips haemorrhoidalis, and Selenothrips rubrocinctus.

In another embodiment of the invention, the plant used in the method for producing a race of an insect pest species exhibiting decreased susceptibility to dsRNA mediated gene suppression is a monocot plant or a dicot plant. In a further embodiment of the invention, the plant is selected from the group consisting of an alfalfa, banana, barley, bean, broccoli, cabbage, brassica, carrot, cassava, castor, cauliflower, celery, chickpea, Chinese cabbage, citrus, coconut, coffee, corn, clover, cotton, a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeon pea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, wheat, and an ornamental plant.

In another embodiment of the invention is a purified and isolated race of a Coleopteran species that is insensitive to endogenous gene suppression when exposed to environmental RNA targeting one or more endogenous essential genes, wherein said race of Coleopteran species is selected from the group of insect genus consisting of a Diabrotica and a Leptinotarsa, and wherein said Diabrotica is further selected from the group consisting of a Northern Corn Rootworm, a Southern Corn Rootworm, a Western Corn Rootworm, a Mexican Corn Rootworm, a Brazilian Corn Rootworm, and a South American Corn Rootworm Complex, and said Leptinotarsa is further characterized as a Colorado Potato Beetle.

In a further embodiment of the invention, the purified and isolated race of a Coleopteran species is used optionally: (a) in assessing frequency of the resistance allele in a field; (b) to map the resistance allele or alleles on the chromosome of said Coleopteran species; and (c) to develop compositions and methods for mediating or overcoming the resistance mechanism.

The purified and isolated race of a Coleopteran species, wherein said race is insensitive to gene suppression when environmental RNA levels targeting an essential gene in said species is provided in the diet of said species from about 0.1 ng/cm$^2$ to about 1,000 ng/cm$^2$ of said diet.

BRIEF DESCRIPTION OF THE SEQUENCES

SEQ ID NO:1 is a nucleic acid sequence encoding the DvSnf7 dsRNA used to create an RNAi resistant Western Corn Rootworm colony.

SEQ ID NO:2 is the DvSnf7 forward primer used to quantify the DvSnf7 expression product in transgenic corn expressing the DvSnf7 transgene.

SEQ ID NO:3 is the DvSnf7 reverse primer used to quantify the DvSnf7 expression product in transgenic corn expressing the DvSnf7 transgene.

SEQ ID NO:4 is a forward primer for amplification of a corn endogenous Actin gene used as a standard for quantification.

SEQ ID NO:5 is a reverse primer for amplification of a corn endogenous Actin gene used as a standard for quantification.

SEQ ID NO:6 is a forward primer for amplification of a corn endogenous Tubulin gene used as a standard for quantification.

SEQ ID NO:7 is a reverse primer for amplification of a corn endogenous Tubulin gene used as a standard for quantification.

DESCRIPTION OF THE INVENTION

Figure 1:
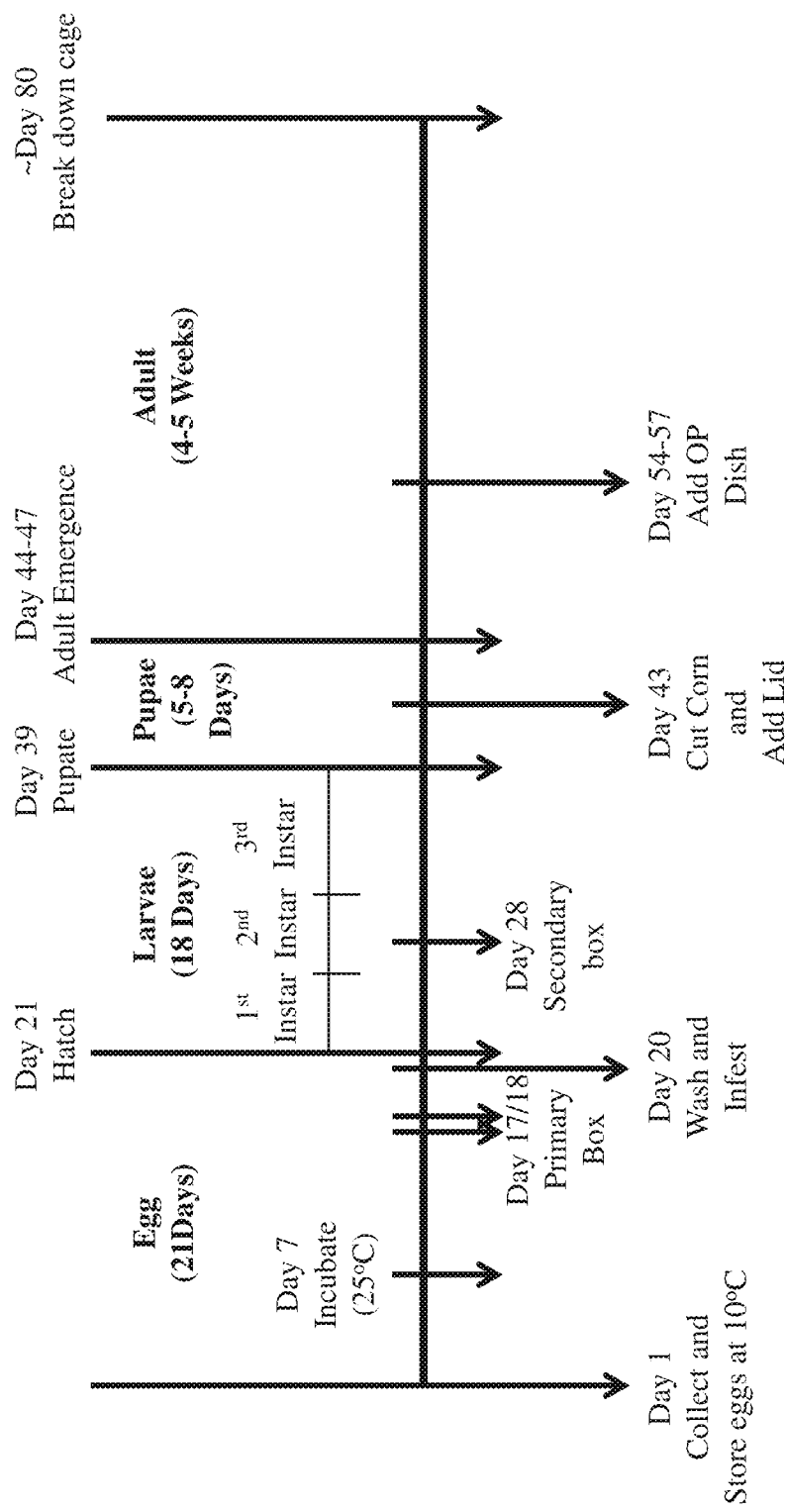
FIG. 1 shows a timeline for an exemplary rearing process used to develop an RNAi resistant Western Corn Rootworm colony (*Diabrotica virgifera virgifera*) and the respective developmental stages from the day of egg collection through the oviposition of the next generation eggs.
Figure 2:
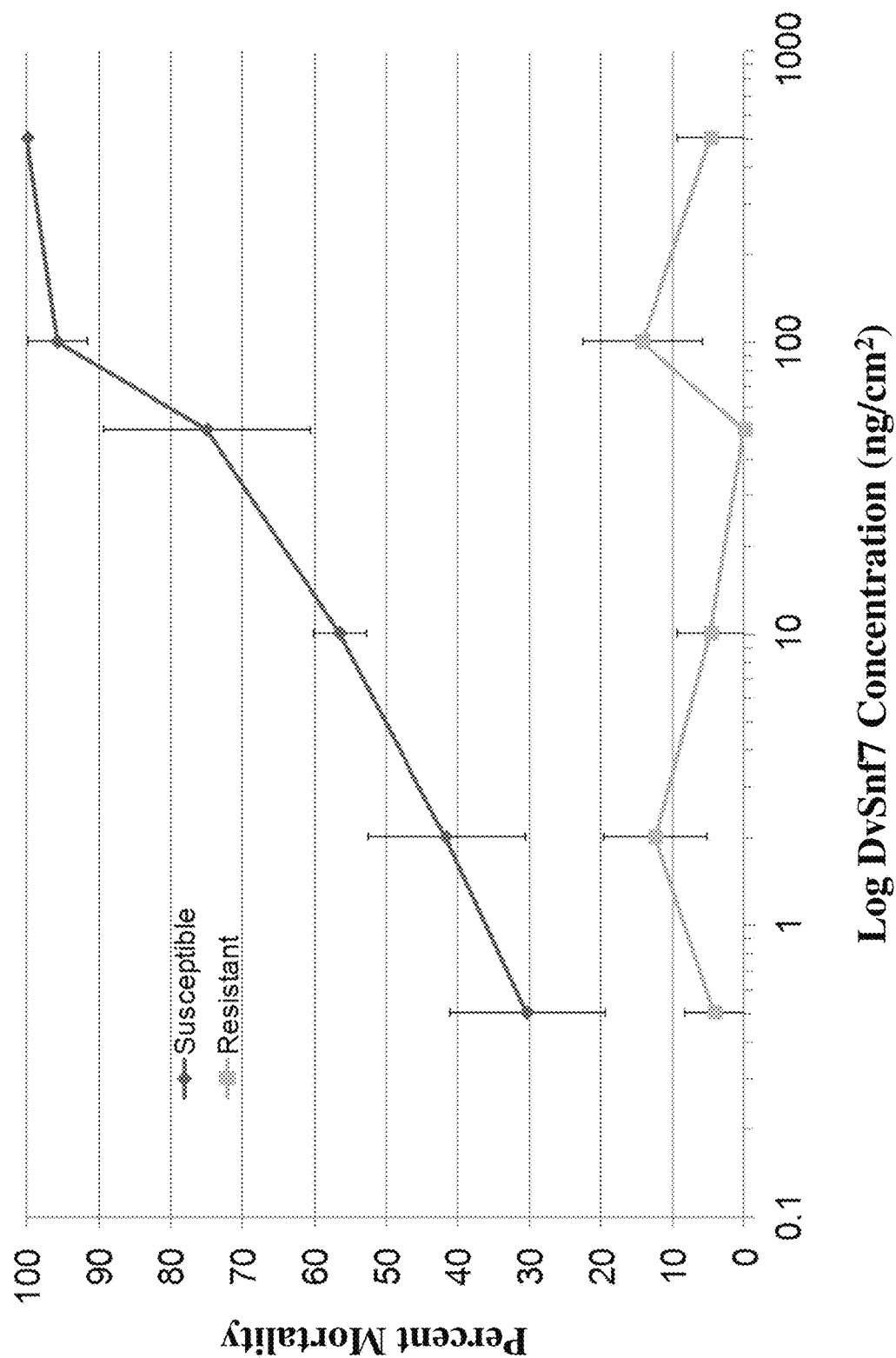
FIG. 2 shows a graph depicting the mean percent mortality of Western Corn Rootworm in both the DvSnf7 (Resistant) and Isoline (Susceptible) colonies in response to increasing concentrations of dsRNA targeting for suppression the gene encoding the DvSnf7 protein. The X axis is shown in a logarithmic scale.

The following is a description of the invention provided to aid those skilled in the art in practicing the present invention. Those of ordinary skill in the art may make modifications and variations in the embodiments described herein without departing from the spirit or scope of the present invention.

Disclosed herein is a method for producing an RNAi resistant colony of an insect pest species. The RNAi resistant colony is produced using colonies of an insect pest species isolated from agricultural fields comprising plants which express an RNAi and agricultural fields that comprise plants that do not express the RNAi. The RNAi resistant colony or colonies can be used through breeding experiments to assess the inheritance of the RNAi resistance trait. In addition, the RNAi resistant colony can be used to assess the frequency of the resistance allele in a field. The resultant RNAi resistant colony can be used in breeding experiments with a dsRNA susceptible colony to map the locus or loci responsible for resistance to the RNAi. Knowledge of the gene or genes involved in conferring such resistance can lead to new strategies of insect management and resistance management. In addition, the RNAi resistant colony can be used to understand the potential or probability for RNAi resistance to develop in an agricultural field comprising plants expressing the RNAi.

The term RNA interference, or RNAi, refers to a collection of biological processes making use of conserved cellular machinery to silence the expression of genes. There are variations in the source of RNA and the specific mechanism through which gene silencing is accomplished, but they are all triggered by the presence of a double-stranded RNA (dsRNA) molecule. The dsRNA is processed into small interfering RNAs (siRNAs), normally around 21-25 bp in length, by the protein Dicer or its homologs and incorporated into a protein complex known as RISC. This complex then uses the siRNA as a template to find and bind to a complementary sequence on a specific messenger RNA. The binding of RISC leads to either the degradation of mRNA or the interruption of mRNA translation into protein. Multiple methods have been used to control insect pest species using RNAi technology. The RNAi can be applied to agricultural fields as a topical spray or other delivery method which results in the deposition of the RNAi on the tissue or tissues from which the insect pest species feeds. Alternatively, transgenic plants can be transformed with expression cassettes that express a dsRNA or a micro-RNA (miRNA) that is directed to disrupt expression of an essential endogenous gene of the insect pest species. For example, expression of the dsRNA DvSnf7 has been shown to be effective in controlling Western Corn Rootworm when expressed in the roots of transgenic corn plants (Moar W, et al. (2017) *Cry3Bb-Resistant Western Corn Rootworm, Diabrotica virgifera virgifera (LeConte) Does Not Exhibit Cross-Resistance to DvSnf7 dsRNA. PLoS ONE* 12(1):e0169175. doi: 10.1371/journal.pone.0169175).

Insect pest species have the ability to adapt to insecticides and other control tactics. The evolution of resistance by the pests can be a threat to the success of insect resistant crops such as those expressing bacterial derived insect toxin proteins and potentially RNAi. Two strategies have been adopted to control the development of resistance to a toxin protein in the field. One is to employ a refuge of plants that do not express the insect toxin protein transgene. The concept underlying this strategy is that most of the rare resistant pests surviving on the toxin protein expressing plants will mate with the relatively abundant susceptible pests from a nearby refuge. If the inheritance of resistance is recessive, the progeny from such mating will die on the toxin protein expressing plants, delaying the evolution of resistance. A second strategy is to provide in the transgenic plant multiple genes with different modes of action (MOA) against an insect pest species. Two or more toxin proteins or one or more toxin proteins and an RNAi having activity against a specific target insect pest species are expressed in the transgenic plant. By providing multiple genes with different MOA, one can significantly increase the time until resistance develops, and extend the durability of the product. Insect pest species have been observed to develop resistance to certain bacterial derived insect toxin proteins (see for example Tabashnik, B., et al. (2013) *Insect resistance to BT crops: lessons from the first billion acres. Nature Biotechnology* 31(6): 510-521).

To date, no study has documented the development of resistance to an RNAi in insect pest species from an agricultural field of transgenic crops expressing an RNAi. Therefore, there is a need for a method of producing an RNAi resistant colony of an insect pest species that which comprise decreased susceptibility to an RNAi or an RNAi expressing plant to better understand the potential for developing resistance to an RNAi. Such an RNAi resistant insect pest species colony could then be used to determine the inheritance (dominant, recessive, or partially dominant or recessive), allele frequency in a field, and mechanism by which resistance has evolved. In addition, the RNAi resistant pest species colony can also be used to determine if there is a fitness cost to the resistance phenotype. Fitness costs occur when fitness on host plants that do not express an insecticidal component is lower for resistant insects than susceptible insects. Such fitness costs can be in the form of lower survival rates, lower copulation rates, lower fecundity, and longer developmental durations. Knowledge gained using the RNAi resistant insect pest species colony can be used to develop better strategies of insect resistance management.

The inventors of this invention disclose a method for developing an RNAi resistant insect pest species colony from insects grown in an agricultural field in which transgenic plants expressing the RNAi are grown. This method can be applied to many insect pest species, particularly those belonging to the orders Coleoptera, Hemiptera, Diptera, and Thysanoptera. Provided in the examples below is a demonstration of the method in which the inventors produce an RNAi resistant colony of Western Corn Rootworm (*Diabrotica virgifera virgifera*, WCR) from WCR grown in a field wherein transgenic corn expressing the dsRNA, DvSnf7 was grown. The resultant DvSnf7 colony is highly resistant to the DvSnf7 dsRNA. The inheritance of resistance was determined to be recessive and is presented in Example 3 below.

The normal rate of mutation in the absence of selection may provide a very small amount of the insect pest species in the field carrying an advantageous mutation that provides resistance to the RNAi. Under high selection, wherein transgenic plants expressing the RNAi are grown and fed on by the insect pest species, the frequency of the resistance allele would be expected to increase. Therefore, collection of an insect pest species to produce an RNAi resistant colony may prove successful if a sufficient number of the insect pest species is present in the field and subjected to selection using the single MOA of the RNAi.

To monitor resistance development in an agricultural field, RNAi resistant insect pest species will typically be collected from one or more agricultural fields in which the evolution of resistance is suspected to have occurred because of an increased number of the insect pest species surviving in the presence of the expressed RNAi. The RNAi resistant insect pest species colony can then be used in reciprocal crosses with insect pest species obtained from each agricultural field to determine the allele frequency which occurs in each agricultural field for the resistance allele. In addition, the RNAi resistant insect pest species colony can be used to build predictive models for resistance development by using such information as the heredity of resistance, the allele frequency from a sample of agricultural fields, and any fitness costs determined to be associated with the resistance phenotype. These predictive models can then be used to develop more effective resistance management programs.

The larvae, nymphs, or adults of a particular insect pest species can be collected at any life stage. Eggs can also be collected from sites. The specific life stage collected will depend upon the particular insect pest species. For example, provided in the examples below is a demonstration of the method using Western Corn Rootworm adults collected from a tented plot of an agricultural field having high Corn Rootworm pressure, in which corn plants expressing the DvSnf7 dsRNA was expressed; and then used in subsequent matings and exposure to the DvSnf7 dsRNA to select for resistant WCR in a colony. A susceptible colony was also derived from a second plot of the same agricultural field in which non-transgenic isoline corn was grown and maintained on non-transgenic isoline corn plants. Collection of adult beetles was necessitated since the WCR first feeds underground as larvae and then emerges as adult beetles after pupation. Those beetles emerging after feeding on the RNAi expressing corn would presumably be resistant or at least a portion of the collected population of the emerged beetles would be resistant to the RNAi. Further selection in the laboratory by presenting the RNAi in the diet of the WCR would further select for resistant WCR.

With respect to other insect pests, the life stage used for collection will largely depend upon the stage at which the insect feeds upon plants expressing the RNAi and non-transgenic plants to obtain two separate colonies used to create the resistant and susceptible colonies; as well as the ease with which to obtain the insect pest. For example, for a Hemipteran insect pest species of Stink Bug, it may be preferable to collect adults since the nymphs will have sufficient time to feed on the RNAi expressing organ, such as a soybean or bean pod. Adult Stink Bugs are capable of flight and collecting them can be accomplished either by shaking the plants to have them drop onto drop clothes or catching them in sweep nets.

As used herein, "effective amount" or "effective concentration" is the amount either in quantity of RNAi or concentration of RNAi that is required to cause significant stunting or mortality to the insect pest species. Significant stunting is stunting that does not permit the insect pest species to advance to the next stage of development and therefore renders the insect functionally dead since it cannot reach adulthood. With respect to the WCR resistant colony described in the examples below, seedlings expressing the DvSnf7 dsRNA were measured for DvSnf7 dsRNA expression using a QuantiGene® assay and expressed as femtograms DvSnf7 RNA per total micrograms RNA (fg DvSnf7/µg RNA). The effective amount of DvSnf7 dsRNA used to produce the DvSnf7 dsRNA resistant colony of WCR was in range of DvSnf7 expression from 743.370 fg DvSnf7/µg RNA to 5634.831 fg DvSnf7/µg RNA, with an average expression of 1871.818 fg DvSnf7/µg RNA. As also presented in the examples below, WCR resistant and susceptible colonies were also assayed using a diet overlay assay in which a solution containing a specific concentration of DvSsf7 dsRNA was placed on top of a WCR diet in agar in 96 well plates. One neonate was used for each well. Twenty four wells were used for each concentration. The neonates were applied to the diet overlay well within twenty four hours after hatching. DvSnf7 dsRNA concentrations ranged from 0 to 500 nanograms DvSnf7 dsRNA per $cm^2$ in concentration steps of 0, 0.5, 2, 10, 50, 100, and 500 nanograms DvSnf7 dsRNA per $cm^2$. The $LC_{50}$ was calculated using the SAS PROC PROBIT statistical software to be at 3.4 nanograms DvSnf7 dsRNA per $cm^2$.

The insect pest species larvae or nymphs are allowed to feed on the RNAi for a period of time sufficient to cause significant stunting or mortality and the surviving insect pest species are selected.

It is intended that reference to a pest, particularly a pest of a crop plant, means insect pest species of crop plants, particularly those that are controlled by the RNAi. However, reference to a pest can also include Coleopteran, Hemipteran, Dipteran, and Thysanopteran insect pest species of plants and animals, as well as nematodes and fungi when toxic agents targeting these pests are co-localized or present together with the RNAi.

As used herein, "resistant colony" or "resistant insect pest species colony" is a colony of an insect pest species that does not demonstrate significant stunting or mortality when fed an effective amount of an RNAi in the insect diet, either from plants expressing the RNAi or an effective concentration of an RNAi in an artificial diet.

As used herein, "susceptible colony" or "susceptible insect pest species colony" is a colony of an insect pest species that demonstrates significant stunting or mortality when fed an effective amount of an RNAi in the insect diet, either from plants expressing the RNAi or an effective concentration of an RNAi in an artificial diet.

As used herein, "non-diapausing" refers to insects of an insect species wherein the normal diapause does not occur. Diapause is a period of suspended or arrested development during an insect's life cycle, and can occur during any stage of development, depending upon the insect species. Each insect species will exhibit diapause at a specific phase of development at a genetically predetermined stage of life. Insect diapause is usually triggered by environmental cues, like changes in daylight, temperature, or food availability. Therefore, environmental cues may control when diapause begins and ends. Diapause can be either obligatory or facultative. Insect species with obligatory diapause will undergo a period of arrested development at the predetermined point in their life cycle, regardless of the environmental conditions. Diapause occurs in every generation. Obligatory diapause is most often associated with insects that have one generation per year. Insects with facultative diapause undergo a period of suspended development only when conditions require it for survival. Facultative diapause is found in most insects which have two or more generations per year. Using wild type insect pest species that are subject to obligatory diapause makes measuring their evolutionary response to selection pressures a very slow process. By using a non-diapausing strain of the insect pest species, breeding and assessment of many generations can be accomplished per year. With respect to insect pest species that are subject to facultative diapause, one can manipulate the environmental conditions such as temperature, light cycle, and nutrition to prevent the occurrence of diapause.

The inventors of the disclosed invention used female WCR derived from the Waterman (WMND) colony originally obtained from the USDA laboratory (Brookings, S. Dak.). WCR undergo obligatory diapause and have one generation per year. In late summer, mated females deposit small gag clutches near the base of corn stalks, where they remain unhatched for the winter. The eggs must go through a cold period before hatching in late spring. The newly hatched larvae move down into the soil and begin feeding on secondary corn roots. The larvae go through three instars and eventually start feeding on and in the primary corn roots. In mid-summer, the larvae pupate in the soil, emerge as adults in five to ten days; and begin feeding on corn silks. The non-diapausing WCR females were mated with WCR males collected from an agricultural field comprising two separate plots; a first plot wherein only transgenic corn plants expressing the DvSnf7 dsRNA were grown, and a second plot wherein only non-transgenic isoline corn plants were grown. The WCR males from each plot were mated with non-diapausing WCR females to create non-diapausing resistant and susceptible WCR colonies. The development of the resistant colony was accelerated as a result of not having to wait for the WCR to come out of diapause.

The disclosed invention can further involve transferring the surviving RNAi resistant insect pest species to a diet of plant not expressing the RNAi or an artificial diet lacking the RNAi to allow the survivors to complete development. Further, the disclosed invention can also comprise allowing the larvae or neonates to feed for one or more generations on plants not expressing the RNAi or an artificial diet lacking the RNAi. This relaxation of selection pressure may be necessary to increase the number of insects over one or more generations to offset mortality that can occur for reasons other than exposure to the RNAi such as crowding effects, heavy soil water saturation, temperature fluctuations, and disease. By relaxing the selection pressure, a larger population of insects carrying the resistance allele can be produced and are available to continue selection without a complete loss of the resistant colony due to effects other than ingestion of the RNAi.

The invention further provides a method for determining the inheritance of resistance in a field-derived colony of an insect pest species that comprises field-evolved resistance to an RNAi. This is accomplished by mating an RNAi resistant insect pest species colony from a field-derived colony of the insect pest species that is susceptible to the RNAi, preferably in reciprocal crosses, and analyzing the mortality rates of the progeny from each mating when grown in the presence of the RNAi. The invention can also comprise backcrossing the progeny of an insect species from each mating to RNAi resistant insects from the resistant insect pest species colony. Such methods can be used to determine if the resistance to the RNAi is dominant, semi-dominant, recessive, or if sex-linkage is involved; and can also be used to determine the number of resistance genes.

In one embodiment of the present invention, the methods for determining the frequency of resistance alleles in a population in which resistance has not evolved comprise collecting an insect pest species from a field, mating virgin adults from the field with adults from the RNAi resistant insect pest species colony, allowing the larvae or nymphs to feed on a diet comprising the RNAi at a concentration that is lethal to the susceptible insect pest species but not lethal to the resistant insect pest species, and demining mortality. Such methods find use, for example, in the development of resistance management strategies.

The methods of the invention include, for example, using such a field-derived colony of insect pest species in methods: for understanding the mechanism of the insect resistance the an RNAi; for evaluating cross-resistance potential of the RNAi with any other RNAi with activity against the insect pest species; to improve resistance monitoring strategies for the insect pest of interest in geographic locations where crop plants expressing the RNAi have been commercialized or are planned to be commercialized; of validating assumptions used in known resistance-risk computer simulation models for crop plants expressing the RNAi; for evaluating alternative refuge deployment strategies for crop plant, such as, for example, seed mixes or refuge-in-a-bag strategies; of investigating whether or not existing insect control tactics will affect the rate at which the insect pest species may develop resistance to transgenic crop plants expressing the RNAi under field conditions; to develop molecular marker technology to monitor for the development of resistance (change in resistant alleles' frequency) to the insecticidal toxin in field populations of the inset pest of interest; and to provide a better understanding on the mode of action of the RNAi in the control of the insect pest species.

The RNAi resistant insect pest species colony can be derived from insect pest species isolated from agricultural fields in which plants expressing the RNAi are grown. Insect pest species which have been shown to have negative impacts upon agricultural crops and ornamental plants, and which have the potential to be controlled using an RNAi expression strategy, are insect pest species from the orders of Coleoptera, Hemiptera, Diptera, and Thysanoptera. In addition, insect pest species from the order Diptera such as Mosquitoes are known to act as vectors for disease in humans and animals. Nearly seven hundred million people get a mosquito borne illness each year resulting in greater than one million deaths (Caraballo, H. (2014) *Emergency Department Management Of Mosquito-Borne Illness: Malaria, Dengue, And West Nile Virus. Emergency Medicine Practice.* 16 (5)). Mosquitos can transmit Malaria, Dengue, West Nile virus, Chikungunya, Yellow fever, Filariasis, Japanese encephalitis, Saint Louis encephalitis, Western Equine encephalitis, Eastern equine encephalitis, Venezuelan equine encephalitis, La Crosse Encephalitis, and Zika. These diseases can also have profound effects on animal livestock as well as pets. Typically, both male and female mosquitos feed on nectar and plant juices. Transgenic plants can be developed that express an RNAi directed to kill the Mosquito species or multiple Mosquito species. Alternatively, the RNAi can be topically applied to plants that are sources for nectar and juices for the Mosquito.

Coleopteran pest species which negatively impact agriculture include, but are not limited to, *Agriotes* spp., *Anthonomus* spp., *Atomaria linearis, Cerotoma* spp., *Chaetocnema tibialis, Chrysomelidae, Cosmopolites* spp., *Curculionidae, Curculio* spp., *Cylas* spp. *Dermestes* spp., *Diabrotica* spp., *Epilachna* spp., *Eremnus* spp., *Lissorhoptrus* spp., *Melolontha* spp., *Orycaephilus* spp., *Otiorhynchus* spp., *Phyllophaga* spp., *Phlyctinus* spp., *Popillia* spp., Japanese beetle (*Popillia japonica*), *Psylliodes* spp., *Rhizopertha* spp., *Scarabeidae, Sitophilus* spp., *Sitotroga* spp., *Tenebrio* spp., *Tribolium* spp. and *Trogoderma* spp, Colorado potato beetle (*Leptinotarsa decemlineata*), *Diabrotica balteata, Diabrotica barberi, Diabrotica beniensis, Diabrotica cristata, Diabrotica curvipustulata, Diabrotica dissimilis, Diabrotica elegantual, Diabrotica emorsitans, Diabrotica graminea, hispanolae, lemniscata, Diabrotica linsleyi, Diabrotica longicornis, Diabrotica milleri, Diabrotica nummularis, Diabrotica occlusa, Diabrotica porracea, Diabrotica scutellata, Diabrotica speciosa, Diabrotica tibialis, Diabrotica trifasciata, Diabrotica undecimpunctata, Diabrotica virgifera, Diabrotica viridula*, Western Corn Rootworm (*Diabrotica virgifera virgifera*, WCR), Northern Corn Rootworm (*Diabrotica barberi*, NCR), Mexican Corn Rootworm (*Diabrotica virgifera zeae*, MCR), Banded Cucumber Beetle (*Diabrotica balteata*, BCR), Southern Corn Rootworm (*Diabrotica undecimpunctata howardii*, SCR), Brazilian Corn Rootworm complex (BCR) consisting of *Diabrotica viridula* and *Diabrotica speciosa*), Crucifer Flea Beetle (*Phyllotreta cruciferae*), Striped Flea Beetle (*Phyllotreta striolata*), Western Black Flea Beetle (*Phyllotreta pusilla*), Maize Billbug (*Sphenophorus maidis*), Southern Corn Billbug (*Sphenophorus callosus*), Cereal Leaf Beetle (*Oulema melanoplus*), Grape Colaspis (*Colaspis brunei*), Sap Beetles (*Carpophilus dimidiatus, C. lugubris*, and *Glischrochilus quadrisignatus*), Seedcorn Beetles (*Stenolophus lecontei* and *Clivina impressifrons*), Southern Corn Leaf Beetle (*Myochrous denticollis*), Sugarcane Beetle (*Euetheola humis rugiceps*), White Grubs (*Cyclocephala* spp. and *Phyllophaga* spp.), and Wireworms (*Aeolus* spp. *Conderus* spp. *Limonius, Hemicrepidius* spp. *Agriotes* spp., and *Melanotus* spp.).

The insect pest species of the order Hemiptera include, but are not limited to, Stink Bugs of the family Pentatomidae: Green Stink Bugs from the genus *Chinavia* (*Chinavia hilaris, Chinavia marginata*, and *Chinavia pensylvanica*), Stink bugs of the genus *Chlorochroa* (*Chlorochroa granulose, Chlorochroa kanei, Chlorochroa ligata, Chlorochroa lineate, Chlorochroa opuntiae, Chlorochroa persimilis, Chlorochroa rossiana, Chlorochroa sayi, Chlorochroa uhleri, Chlorochroa belfragii, Chlorochroa faceta, Chlorochroa osborni, Chlorochroa saucia*, and *Chlorochroa senilis*), Southern Green Stink Bug (*Nezara viridula*), Stink Bugs from the genus *Edessa* (*Edessa meditabunda, Edessa bifida*, and *Edessa florida*), the Neotropical Brown Stink Bug (*Euschistus heros*), stink bugs from the genus *Euschistus* (*Euschistus acuminatus, Euschistus biformis, Euschistus conspersus, Euschistus crenator, Euschistus egglestoni, Euschistus ictericus, Euschistus inflatus, Euschistus latimarginatus, Euschistus obscures, Euschistus politus, Euschistus quadrator, Euschistus sevus, Euschistus strenuous, Euschistus tristigmus*, and *Euschistus variolarius*), Brown Marmorated Stink Bug (*Halyomorpha halys*), Red-Shouldered Stink Bug (*Thyanta accerra*), stink bugs of the genus *Thyanta* (*Thyanta calceata, Thyanta custator, Thyanta pallidovirens, Thyanta perditor, Thyanta maculate*, and *Thyanta pseudocasta*), the Green Belly Stink Bug (*Dichelops melacanthus*) and other stink bugs of the genus *Dichelops* (*Dichelops avilapiresi, Dichelops bicolor, Dichelops dimidatus, Dichelops furcatus, Dichelops furcifrons, Dichelops lobatus, Dichelops miriamae, Dichelops nigrum, Dichelops peruanus, Dichelops phoenix*, and *Dichelops saltensis*), the Red Banded Stink Bug (*Piezodorus guildinni*) as well as *Piezodorus lituratus*; insect pest species of the family of Plataspidae such as Kudzu Bug (*Megacopta cribraria*); insect pest species of the family Lygaeidae such Chinch Bug (*Blissus leucopterus leucopterus*); insect pest species of the family Miridae such as Tarnished Plant Bug (*Lygus lineolaris*) and Western Tarnished Plant Bug (*Lygus hesperus*); Aphid (Hemiptera: Aphidae) species such as Bean aphid (*Aphis fabae*), Cabbage aphid (*Brevicoryne brassicae*), Green peach aphid (*Myzus persicae*), Melon (cotton) aphid (*Aphis gossypii*), Potato aphid (*Macrosiphum euphorbiae*), Green apple aphid (*Aphis pomi*), Leaf curl plum aphid (*Brachycaudus helichrysi*), Mealy plum aphid (*Hyalopterus pruni*), Rosy apple aphid (*Dysaphis plantaginea*), Woolly apple aphid (*Eriosoma lanigerum*), Ash leaf curl aphid (*Prociphilus* spp.), Crapemyrtle aphid (*Sarucallis kahawaluokalani*), Giant conifer aphid (*Cinara* spp.), Hackberry woolly aphid (*Shivaphis celti*), Oleander aphid (*Aphis nerii*), Rose aphid (*Macrosiphum rosae*), and Tuliptree aphid (*Illinoia liriodendra*); Scale insect pest species such as California red scale (*Aonidiella aurantii*), Cycad scale (*Furchadaspis zamiae*), Euonymus scale (*Unaspis euonymi*), Greedy scale (*Hemiberlesia rapax*), Latania scale (*Hemiberlesia lataniae*), Minute cypress scale (*Carulaspis minima*), Obscure scale (*Melanaspis obscura*), Oleander scale (*Aspidiotus nerii*), Olive scale (*Parlatoria oleae*), Oystershell scale (*Lepidosaphes ulmi*), Purple scale (*Lepidosaphes beckii*), San Jose scale (*Quadraspidiotus perniciosus*), and Walnut scale (*Quadraspidiotus juglansregiae*); and Whitefly species such as Ash whitefly (*Siphoninus phillyreae*), Greenhouse whitefly (*Trialeurodes vaporariorum*), Banded winged whitefly (*Trialeurodes abutilonea*), Iris whitefly (*Aleyrodes spiraeoides*), Citrus whitefly (*Dialeurodes citri*), Mulberry whitefly (*Tetraleurodes mori*), Crown whitefly (*Aleuroplatus coronata*), Sweetpotato whitefly (*Bemisia tabaci*), Giant whitefly (*Aleurodicus dugesii*), and Woolly whitefly (*Aleurothrixus floccosus*).

The insect pest species of Diptera include, but are not limited to, Mosquito (Diptera: Culicidae) species, *Anopheles* spp., Malaria mosquito (*Anopheles quadrimaculatus*), *Anopheles walker, Anopheles freeborni, Aedes* spp., Yellow Fever Mosquito n(*Aedes aegypti*), Asian Tiger Mosquito (*Aedes albopictus*), *Aedes Canadensis, Aedes sollicitans, Aedes nigromaculis, Culex* spp., *Culex erraticus, Culex* nigripalpus, Culex stigmatosoma, House Mosquito (*Culex pipiens*, also called *Culex fatigans*), *Culex salinarius, Culex tarsalis, Culiseta* spp., *Culiseta incidens, Culiseta inornata, Culiseta melanura, Mansonia* spp., *Mansonia titillans, Coquillettidia* spp., *Coquillettidia pertubans, Psorophora* spp., *Psorophora ciliate, Psorophora columbiae* (also called *Psorophora confinnis*), *Psorophora columbiae, Psorophora cyanescens, Psorophora ferox*, and *Psorophora signipennis*: Gall Midges belonging to the Family Cecidomyiidae, Hessian fly (*Mayetiola destructor*), Wheat blossom midge (*Sitodiplosis mosellana*), the Asian rice gall midge (*Orseolia oryzae*), African rice gall midge (*Orseolia oryzivora*), Coffee flower midge (*Dasyneura coffeae*), Soybean pod gall midge (*Asphondylia yushimai*), Pine needle gall midge (*Thecodiplosis japonensis*), Lentil flower midge (*Contarinia lentis*), Lucerne flower midge (*Contarinia medicaginis*), Alfalfa sprout midge (*Dasineura ignorata*), Black locust tree gall midge (*Obolodiplosis robiniae*), Swede midge (*Contarinia nasturtii*), Brassica pod midge (*Dasineura brassicae*), Pear midge (*Contarinia pyrivora*), Raspberry cane midge (*Resseliella theobaldi*), Ornamental fig midge (*Horidiplosis ficifolii*), Rosette gall midge (*Rhopalomyia solidaginis*), *Porrcondylini* spp., *Lestremia* spp., *Lestodiplosis* spp., *Acaroletes* spp., *Aphidoletes* spp., *Lestodiplosis* spp., *Acaroletes* spp., *Aphidoletes* spp., and *Arthrocnodax* spp.; pest species of Leaf-Miners belonging to the family Agromyzidae, *Agromyza* spp., *Agromyza abiens, Agromyza albipennis, Agromyza alnivora, Agromyza ambigua, Agromyza apfelbecki, Agromyza cinerascens, Agromyza drepanura, Agromyza frontella, Agromyza intermittens, Agromyza luteitarsis, Agromyza megalopsis, Agromyza nana, Agromyza nigrella, Agromyza nigrociliata, Agromyza oryzae, Agromyza parvicornis, Agromyza rondensis, Agromyza yanonis; Melanagromyza* spp., *Melanagromyza aeneoventris, Melanagromyza lappae, Melanagromyza albocilia, Melanagromyza minimoides, Melanagromyza obtuse, Melanagromyza sojae, Melanagromyza Hendel, Melanagromyza splendid, Melanagromyza ricini, Melanagromyza obtuse, Melanagromyza aenea; Ophiomyia* spp., Asparagus miner (*Ophioinyia simplex*); *Lirionvza* spp., South American leaf miner (*Liriomyza huidobrensis*), American serpentine leaf miner (*Liriomyza trifolii*), Vegetable leaf miner (*Liriomyza sativae*), Tomato leaf miner (*Liriomyza bryoniae*), Serpentine leaf miner (*Liriomyza brassicae*); *Napomyza* spp., *Napomyza lateralis, Napomyza bellidis, Napomyza carotae, Napomyza cichorii,* and *Phytomyza* spp., *Phytomyza ilicis, Phytomyza spondylii, Phytomyza ilicicola, Phytomyza (Napomyza) gymnostoma, Phytomyza horticola,* and *Phytomyza aquilegivora*; and Root Maggots belonging to the family Anthomyiidae, *Delia* spp., Onion fly (*Delia antiqua*), Wheat bulb fly (*Delia coarctata*), Turnip root fly (*Delia floralis*), Seed corn maggot (*Delia platura*), and Cabbage root fly (*Delia radicum*).

Thysanopteran insect pest species (Insecta: Thysanoptera) which negatively impact agriculture include, but are not limited to, Western Flower Thrips (*Frankliniella occidentalis*), Eastern Flower Thrips (*Frankliniella tritici*), Corn Thrips (*Frankliniella williamsi*), Florida Flower Thrips (*Frankliniella bispinosa*), Tobacco Thrips (*Frankliniella fusca*), Tomato Thrips (*Frankliniella schultzei*), Soybean Thrips (*Sericothrips variabilis*), Cuban Laurel Thrips (*Gynaikothrips ficorum*), Weeping Fig Thrips (*Gynaikothrips uzeli*), Tabebuia Thrips (*Holopothrips tabebuia*), Basswood Thrips (*Thrips calcaratus*), Melon or Palm Thrips (*Thrips palmi*), Gladiolus Thrips (*Thrips simplex*), Onion Thrips (*Thrips tabaci*), Citrus Thrips (*Scirtothrips citri*), Chilli Thrips (*Scirtothrips dorsalis*), Avocado Thrips (*Scirtothrips perseae*), Orchid or Anthurium Thrips (*Chaetanaphothrips orchidii*), Poinsettia thrips (*Echinothrips americanus*), Pear Thrips (*Taeniothrips inconsequens*), Bean Thrips (*Caliothrips fasciatus*), Greenhouse Thrips (*Heliothrips haemorrhoidalis*), and Redbanded Thrips (*Selenothrips rubrocinctus*).

EXAMPLES

In view of the foregoing, those of skill in the art should appreciate that changes can be made in the specific aspects which are disclosed and still obtain a like or similar result without departing from the spirit and scope of the invention. Thus, specific structural and functional details disclosed herein are not to be interpreted as limiting. It should be understood that the entire disclosure of each reference cited herein is incorporated within the disclosure of this application.

Example 1

Rearing of DvSnf7 Resistant and Control Western Corn Rootworm (*Diabrotica virgifera virgifera*)

This example describes the entire rearing process used to develop an RNAi resistant Western Corn Rootworm colony (*Diabrotica virgifera virgifera*) as described below in Example 2.

Non-diapausing Western Corn Rootworm (WCR) colonies were derived from crossing field collected male WCR adults with non-diapausing females adult WCR from the Waterman (WMND) colony originally obtained from the USDA laboratory (Brookings, S. Dak.). Non-diapausing WCR colony-derived eggs require no extended period of cold storage prior to incubation to induce hatching. FIG. 1 depicts the entire rearing timeline which is approximately eighty days and shows the relationship of each step with respect to the life cycle of WCR.

Eggs are collected in oviposition (OP) dishes. OP dishes are made by mixing water with milled soil (Crop Characteristics, Farmington, Minn.) until solid, but moist in consistency. The soil mixture is aliquoted into 100 mm×15 mm Petri dishes. The OP's are stored at 10° C.

To collect WCR eggs OP dishes are added to cages in which the adult WCR emerge. The OP dishes are covered with aluminum foil that has been folded to resemble a fan. The aluminum foil shields the OP dish from light but allows the female adults to easily access the OP dish and oviposit their eggs. The WCR adults usually emerge forty-four to forty-seven days into the life cycle illustrated in FIG. 1. The adults are fed water and a diet comprised of premixed Bio-Serv diet (Product No. F9760B, Frenchtown, N.J.), corn meal and honey. Water is presented in bottles with a dental wick stuck through the cap. Ten days after the first adult emergence (Day 54-57) the OP dishes covered by the aluminum foil fan are added to the cage. The female WCR adults are allowed to oviposit eggs. The OP dishes are replaced every Monday, Wednesday, and Friday. After collection, the OP dish is sprayed with de-ionized (DI) water, dusted with a layer of milled soil, and then sprayed an additional time to moisten the new soil. The OP dishes are wrapped in paraffin and then stored at 1° C. to prevent hatching of the eggs until needed.

After all of the OP dishes have been collected from each colony, the OP dishes are incubated at 25° C. On approximately day ten to thirteen following the initial incubation the OP dish is placed inside two, eight-inch coffee filters. The soil is sprayed with DI water if the soil is dry to the touch. The coffee filters and OP dish are placed in Solo clear plastic food containers (16 oz/473 ml). The lid of the container is snapped onto the container and around ten holes are punched through the lid to all air to enter and prevent the accumulation of excess moisture.

The neonates spend the first, and part of the second instar in a "primary box" (Newspring VERSAtainer NC-888-B 38 oz.) that is eight and one half inches long, six inches wide, and two inches high. Seeds of corn plants that express the DvSnf7 dsRNA or non-transgenic isoline plants are pre-germinated in a plastic beaker, covered with water five days prior to the expected day of egg hatch. Approximately sixty seeds are pre-germinated for each primary box needed. On the following day, four days before the expected egg hatch, the water is drained of and the seeds are washed three times. A thin layer of steam sterilized soil (Metromix 200, Hummert International, Topeka, Kans.), approximately three quarters of an inch is spread out in the primary box. The pre-germinated seeds are evenly spread out over the soil. More soil is added over the seed to the top of the primary box. The primary boxes are watered liberally and stored in growth chambers set to a twelve hour day length and 25° C. Water is added daily as needed.

Twenty days after the initial day of incubation of the OP dishes at 25° C., the eggs are washed from the soil and used to infest the emerging corn seedlings. Each primary box is infested with no more than 200 eggs per primary box to minimize density-dependent mortality. At day twenty one, the eggs usually hatch and the larvae will drill into the soil to feed on the corn seedling roots. The larvae are immediately attracted to corn roots by the emission of $CO_2$ from the root tips and begin feeding.

Twenty eight days from the initial egg incubation, the soil mats from the primary boxes are transferred to secondary boxes. The larvae, if alive, will be in the second instar of development at the time of transfer. Secondary boxes are made using large clear plastic boxes (Pioneer Plastics No. 395C, Dixon, Ky.) that measure twelve and one-half inches in length, ten and one sixteenth inches wide, and three and thirteen sixteenths inches high. Six days after infestation, more seeds are pre-germinated as described above. The following day, the seeds are drained and rinsed three times. A layer of sterile soil (Metromix 200) is put into the bottom of the box. The entire soil with seedlings, which is now a mat from the primary box due to the root mass, is transferred to the secondary box. Two primary box soil mats are moved into each secondary box. The primary boxes are tapped over the secondary box to transfer any larvae that were not within the soil mats. Pre-germinated seeds are evenly dispersed around the perimeter of the mats and soil is added on top to level of the soil in the primary box mats. The secondary mats are put into the growth chamber and the soil is watered sufficiently to keep the soil wet but not flooded. About a week before the corn seedlings are cut down, watering is reduced to allow the soil to begin drying and dry down until there is a little moisture for the adults to emerge.

Forty-three days after the initial egg incubation, the corn seedlings are cut down, leaving the roots intact in the soil. The secondary box is covered with the lid supplied with the box. Adults WCR will begin to emerge a day or so later.

As WCR beetles emerge, they are transferred to cages. Male WCR beetles usually emerge before females. No more than five hundred beetles should be placed in each cage after collection on Monday or seven hundred by Tuesday. This helps maximize egg production by ensuring a good sex ratio in each cage. The total number of beetles added to a cage over time does not exceed one thousand. OP dishes are added to the cage as described above ten days after the first emergence. Food is added every Monday and Friday as described above. OP dishes are replaced every Monday, Wednesday, and Friday as described above. Egg production begins to fall off after three to four weeks of OP collection. The cages are removed and frozen. Remaining live beetles are collected and stored at –80° C. for use in molecular assays.

Example 2

Development of a DvSnf7 dsRNA Resistance Western Corn Rootworm Colony

This example describes the method used to create a DvSnf7 dsRNA resistant colony of WCR using high selective pressure to select for WCR beetles resistant to DvSnf7.

Adult WCR beetles were collected from a field plots experiencing high WCR pressure which exceeded the economic threshold for application of insecticides in Waterman, Ill. One plot was tented to prevent beetle escape and transgenic plants expressing the DvSnf7 dsRNA (SEQ ID NO:1) were planted. The number of WCR eggs per plant in this highly infested area was estimated to be five hundred to more than one thousand per plant. Approximately three thousand five hundred transgenic plants were planted in the tented plot. The estimated number of larvae that would undergo selection from the DvSnf7 dsRNA expressing corn roots was between 1.75 to 3.5 million. A second plot was used to grow a non-transgenic isoline of corn. The isoline plot consisted of non-transgenic isoline corn plants that were planted surrounding the tented plot.

Samples of seedlings expressing DvSnf7 were taken for analysis to measure the level of DvSnf7 dsRNA expression using a QuantiGene® assay. Total RNA was extracted from frozen roots of DvSnf7 expressing seedlings. The DvSnf7 forward and reverse primers presented as SEQ ID NOs:2 and 3, respectively were used to amplify the DvSnf7 transcript. Two endogenous corn genes were also used as standards to normalize the expression data, Actin (primers SEQ ID NOs:4 and 5) and Tubulin (primers SEQ ID NOs:6 and 7). Table 1 below shows the amount of DvSnf7 dsRNA expressed in the transgenic corn seedling roots sampled at V1 through V3 stage and quantified as femtograms (fg) of DvSnf7 dsRNA per microgram (pg) total RNA (fg DvSnf7/ug RNA). The range of DvSnf7 expression was from 743.370 fg DvSnf7/ug RNA to 5,634.831 fg DvSnf7/ug RNA, with an average expression of 1871.818 fg DvSnf7/μg RNA. The median expression of DvSnf7 for each growth stage (V1, V2, and V3) ranged from 1,593-2,192 fg DvSnf7/ug RNA. DvSnf7 expression was also measured in ten root samples of non-transgenic isoline seedlings and was at background levels.

TABLE 1

Fentograms of DvSnf7 dsRNA expressed per nanogram total RNA in transgenic DvSnf7corn plant roots.

| Sample | Growth Stage | fg DvSnf7 per pg RNA | Sample | Growth Stage | fg DvSnf7 per μg RNA |
|---|---|---|---|---|---|
| 1 | V1 | 3748.939 | 16 | V2 | 2190.635 |
| 2 | V1 | 1685.631 | 17 | V3 | 998.052 |
| 3 | V1 | 5634.831 | 18 | V3 | 1398.12 |
| 4 | V1 | 2802.803 | 19 | V3 | 4289.338 |
| 5 | V1 | 1806.127 | 20 | V3 | 1086.07 |

TABLE 1-continued

Fentograms of DvSnf7 dsRNA expressed per nanogram total RNA in transgenic DvSnf7corn plant roots.

| Sample | Growth Stage | fg DvSnf7 per pg RNA | Sample | Growth Stage | fg DvSnf7 per µg RNA |
|---|---|---|---|---|---|
| 6 | V1 | 1260.595 | 21 | V3 | 1521.491 |
| 7 | V1 | 1105.063 | 22 | V3 | 1489.47 |
| 8 | V1 | 936.83 | 23 | V3 | 1155.767 |
| 9 | V2 | 1322.463 | 24 | V3 | 743.37 |
| 10 | V2 | 1306.986 | 25 | V3 | 1396.295 |
| 11 | V2 | 2946.107 | 26 | V3 | 1550.331 |
| 12 | V2 | 1163.923 | 27 | V3 | 3256.983 |
| 13 | V2 | 1678.741 | 28 | V3 | 1580.108 |
| 14 | V2 | 1258.777 | 29 | V3 | 1426.416 |
| 15 | V2 | 1588.815 | 30 | V3 | 1825.471 |

Three hundred and fifty adult beetles were collected after emergence from the soil from the tented plot containing the DvSnf7 transgenic corn. From the non-transgenic isoline plot, five hundred adult beetles were collected after emergence. Male beetles from the DvSnf7 and isoline plots were mated with non-diapausing females adult WCR from the Waterman (WMND) colony originally obtained from the USDA laboratory (Brookings, S. Dak.) producing F1 progeny eggs. The F1 progeny and subsequent generations from the DvSnf7 plot are herein referred to as the "DvSnf7 colony." The F1 progeny and subsequent generations derived from the isoline plot are herein referred to as the "Isoline colony." F1 DvSnf7 and Isoline colony eggs were collected in OP dishes after mating as described above. The resulting DvSnf7 and Isoline colony eggs were incubated at 25° C. and used to infest isoline only corn seedlings in the primary and secondary boxes as described above. DvSnf7 and Isoline colony eggs and pupae were grown in different primary and secondary boxes to maintain the integrity of each colony.

The F2 through F11 generations of the isoline colony were used to infest isoline corn seedlings. Generations of F2 through F4 of the DvSnf7 colony were used to infest DvSnf7 expressing corn seedlings. The F5 through F7 generations of the DvSnf7 colony were used to infest non-transgenic isoline corn seedlings. The relaxing of selection pressure in F5 through F7 was done to assure there would be a large enough population to continue driving selection since the numbers emerged in F5 was very low. Generations F7 through F11 of the DvSnf7 colony were used to infest transgenic DvSnf7 expressing corn seedlings. From F11on, the colony was selected on DvSnf7 dsRNA expressing corn every other generation.

Adult emergence was observed for the DvSnf7 colony for each generation. The percent adult emergence from each generation is shown in Table 2 below. Table 2 also includes data from the F7 generation DvSnf7 colony WCR fed on non-transgenic isoline seedling roots to compare emergence data to the F7 generation DvSnf7 colony fed on DvSnf7 transgenic seedling roots. As can be seen in Table 2 below only 16.92% of the DvSnf7 colony neonates used to infest the DvSnf7 transgenic seedlings emerged as adults, while greater than 50% of the DvSnf7 colony neonates emerged as adults when fed non-transgenic isoline roots. Thus a portion of the F7 generation DvSnf7 colony WCR neonates were resistant to the DvSnf7 dsRNA.

TABLE 2

Number of WCR neonates infested, adults emerged, and percent adult emergence for F2 through F11 generations of the DvSnf7 colony.

| Generation | Plant | Neonates infested | Emerged Adults | Mean Adult Emergence |
|---|---|---|---|---|
| F2 | DvSnf7 | 27624 | 1277 | 4.62% |
| F3 | DvSnf7 | 690 | 209 | 30.29% |
| F4 | DvSnf7 | 1075 | 91 | 8.47% |
| F5 | Isoline | 181 | 126 | 69.61% |
| F6 | Isoline | 1500 | 182 | 12.13% |
| F7 | Isoline | 1001 | 518 | 51.75% |
| F7 | DvSnf7 | 1129 | 191 | 16.92% |
| F8 | DvSnf7 | 1835 | 723 | 39.40% |
| F9 | DvSnf7 | 4448 | 1042 | 23.43% |
| F10 | DvSnf7 | 5074 | 349 | 6.88% |
| F11 | DvSnf7 | 5883 | 957 | 16.27% |

Larvae were first evaluated in F6 for resistance using quantitative real time PCR for suppression of the DvSnf7 transcript. Larvae from both the DvSnf7 dsRNA resistant and susceptible colonies were fed corn roots expressing DvSnf7 dsRNA or non-transgenic isoline corn roots. After feeding the guts were removed from the insects and analysis was performed on both the gut and carcasses. Of twelve resistant larvae ten showed no significant decrease in DvSnf7 transcript when fed transgenic roots expressing the DvSnf7 dsRNA in both carcass and gut tissues. All susceptible larvae which fed on transgenic roots expressing the DvSnf7 dsRNA showed a significant reduction in DvSfn7 transcript.

The only food source for the DvSnf7 WCR colonies in generations F2 through F4 and generations F7 through F11 was DvSnf7 expressing root tissues. Adults were able to emerge from those generations after feeding on the DvSnf7 dsRNA demonstrating the DvSnf7 colony developed resistance to the DvSnf7 dsRNA. In order to confirm resistance, F10 generation DvSnf7 (Resistant) and Isoline (Susceptible) colonies were assayed for mortality on food media overlaid with DvSnf7 dsRNA. The DvSnf7 dsRNA Susceptible and Resistant WCR were assayed in ninety-six well plates. Twenty-four wells were used for each concentration with one WCR larvae per well. Concentrations of DvSnf7 dsRNA ranged from zero nanograms per $cm^2$ to five hundred nanograms per $cm^2$. WCR neonates were applied to each well within twenty-four hours after hatching. Table 3 and FIG. 2 show the mean percent mortality of WCR in both the DvSnf7 (Resistant) and Isoline (Susceptible) colonies in response to increasing concentrations of DvSnf7 dsRNA.

TABLE 3

Mean percent mortality of DvSnf7 Susceptible and Resistant colonies.

| Overlay concentration | Susceptible | | Resistant | |
|---|---|---|---|---|
| (ng/$cm^2$) | Mean | SE | Mean | SE |
| 0 | 30.36 | 3.72 | 4.17 | 4.17 |
| 0.5 | 30.36 | 10.86 | 4.17 | 4.17 |
| 2 | 41.67 | 11.02 | 12.50 | 7.22 |
| 10 | 56.55 | 3.62 | 4.76 | 4.76 |
| 50 | 75.00 | 14.43 | 0.00 | 0.00 |
| 100 | 95.83 | 4.17 | 14.29 | 8.25 |
| 500 | 100.00 | 0.00 | 4.76 | 4.76 |

As can be seen in Table 3 above, the susceptible isoline colony experienced increasing mortality as the concentration of DvSnf7 dsRNA was increased. The $LC_{50}$ was calculated using the SAS PROC PROBIT statistical software to be at 3.43 nanograms DvSnf7 dsRNA per $cm^2$. For the resistant DvSnf7 colony increasing the concentration of DvSnf7 dsRNA had little to no effect. An $LC_{50}$ could not be calculated for this colony because mortality in this experiment did not reach fifty percent or higher. Selection of WCR on a single mode of action (MOA) can result in resistance developing in a population of WCR. Selection using the single MOA of DvSnf7 resulted in the development of a DvSnf7 resistant WCR colony.

Later diet overlay feeding studies demonstrated the resistant colony was able to survive a concentration of one thousand nanograms DvSnf7 dsRNA per $cm^2$.

The development of a colony of Western Corn Rootworm which exhibits such a high degree of resistance to the DvSnf7 dsRNA presents several opportunities for investigation and use of colonies resistant to transgenic corn events expressing DvSnf7. Because the resistance to DvSnf7 was developed from WCR exposed in the field to transgenic corn plants expressing DvSnf7, and subsequently reared on the transgenic roots of seedlings expressing DvSnf7; the DvSnf7 Resistant colony more closely reflects tolerance which naturally develops through repeated field exposure.

Example 3

Determination of Inheritance of the DvSnf7 dsRNA Resistance Phenotype

This example describes the determination of inheritance of the DvSnf7 resistant phenotype and provides data showing the phenotype is inherited as a recessive trait.

To evaluate the dominance of resistance, F1 progeny from reciprocal crosses between resistant and susceptible populations (resistant ♀ x susceptible ♂ and resistant ♂ x susceptible ♀) were evaluated in diet bioassay along with resistant and susceptible insects. Each cross had eighty males and eighty females. Separate cages were made for resistant and susceptible adults with similar number of males and females collected from the same generation that was used for making reciprocal crosses. Concentration mortality data was analyzed using Gompertz model from SAS PROC PROBIT with the option OPTC for correcting the natural rate of mortality. $LC_{50}$ with a 95 percent confidence interval (CI), slopes and standard errors were calculated. Degree of dominance (D) was calculated using a formula developed by B. F. Stone (Stone, B. F., *A Formula for Determining Degree of Dominance in Cases of Monofactorial Inheritance to Resistance to Chemicals*, Bull World Health Organ. 1968; 38(2):325-6), $$D=(2X_2-X_1-X_3)/(X_1-X_3),$$

where $X_2$ is the mean of the $LC_{50}$ values of reciprocal crosses and $X_1$ and $X_3$ are $LC_{50}$ values of resistant and susceptible populations respectively. Since the $LC_{50}$ value for the resistant population could not be determined, the highest concentration (500 ng/$cm^2$) used for resistant insects was used in the calculations. The value of D ranges from −1 to 1, where D=1 indicates complete dominance; 0<D<1 indicates incomplete dominance; −1<D<0 indicate incomplete recessive and D=−1 indicates complete recessive.

Figure 3:
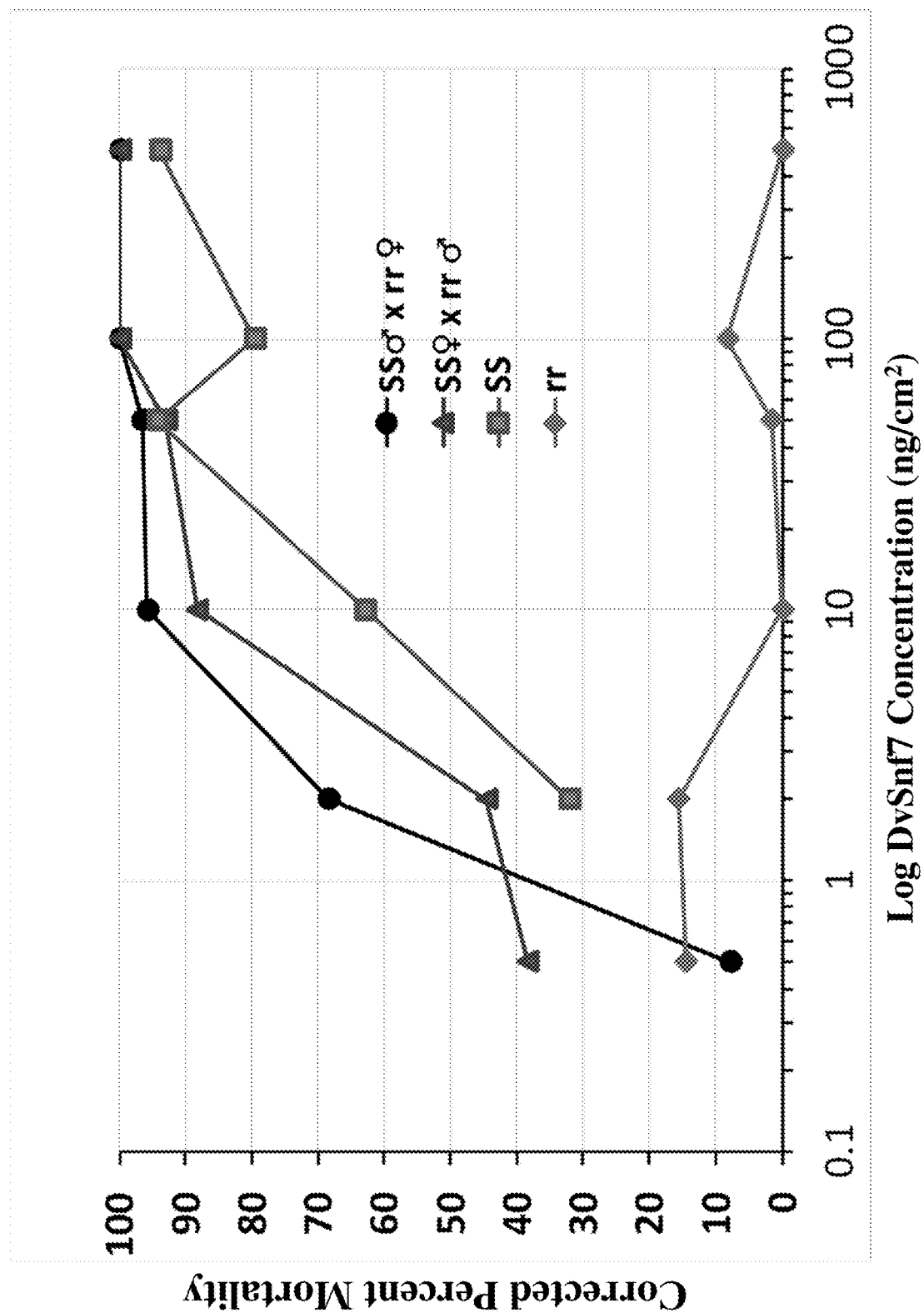
FIG. 3 shows a graph depicting the corrected percent mortality the DvSnf7 (Resistant) and Isoline (Susceptible) colonies as well as reciprocal crosses between susceptible males with resistant females, and resistant males with susceptible females in response to increasing concentrations of dsRNA targeting for suppression the gene encoding the DvSnf7 protein. The X axis is shown in a logarithmic scale.

Table 4 shows the data derived from the concentration responses of the Resistant and Susceptible reciprocal crossed of WCR DvSnf7 dsRNA overlaid on an artificial diet. FIG. 3 shows the dose response curves for the Resistant, Susceptible and Reciprocal crosses.

TABLE 4

Concentration response of Resistant (rr), Susceptible (SS), and the reciprocal crosses populations (resistant ♀ y x susceptible ♂ and resistant ♂ x susceptible ♀)

| Population | N | Slope ± SE | $LC_{50\ in\ ng/cm}^2$ (95% CI) | Resistance ratio | $\chi^2$ | P value |
|---|---|---|---|---|---|---|
| SS | 105 | 1.39 ± 0.54 | 3.70 (0-15.8) | — | 13.5 (11) | 0.2616 |
| rr | 253 | NC* | >500 | >130 | NC* | NC* |
| SS♀ x rr ♂ | 139 | 2.05 ± 0.61 | 1.48 (0.1-4.40) | 0.4 | 9.2 (16) | 0.9047 |
| SS♂ x rr ♀ | 254 | 3.26 ± 0.83 | 1.42 (0.56-2.66) | 0.38 | 22.2 (28) | 0.7734 |

*NC - Not calculated

The fiducial limits from the Gompertz model for the susceptible and F1's were overlapped, indicating the three groups are not significantly different at alpha=0.05. $LC_{50}$ for resistant population was not run since the mortality never reached 50%. Using the data provided in Table 4 above, the value of D was calculated as −1 indicating the inheritance of the resistance trait is completely recessive. As can be seen in FIG. 3, the slopes of Susceptible (SS), and the reciprocal crosses (resistant ♀ x susceptible ♂ and resistant ♂ x susceptible ♀) are very similar. The mortality curves generated in the bioassay indicate that resistance to the DvSnf7 dsRNA is recessive and autosomal.

Using homozygous recessive DvSnf7 resistant WCR such as those developed by the process described above can be used to estimate allele frequency in the field through single pair matings of field collected WCR individuals with the DvSnf7 resistant individuals from the resistant DvSnf7 colony.

Example 4

Determination of Allele Frequency of DvSnf7 dsRNA Resistance in a Field Infested with WCR This example describes the determination of the DvSnf7 resistant allele frequency in a field infested with WCR.

To determine the DvSnf7 resistant allele frequency, single pair mating families of WCR were produced by crossing field collected male adult beetles with unmated females from the DvSnf7 resistant colony. A total of two hundred and twelve families were made from the crosses. Eighty-six of the families laid enough eggs to use in a diet overlay assay. The $F_1$ neonates were exposed to a diet overlay containing 1,000 ng/$cm^2$ DvSnf7 dsRNA. A second group of the $F_1$ neonates was reared on a diet without the DvSnf7 dsRNA. Out of the eighty-six families, only four families produced neonates that were resistant to the DvSnf7 dsRNA. Table 5 below shows the percent survival of the WCR neonates in the presence or absence of the DvSnf7 dsRNA in the diet of the WCR colonies.

TABLE 5

Percent survival of WCR neonates.

| | Percent Survival | |
|---|---|---|
| Family ID | 1000 ng/$cm^2$ | 0 ng/$cm^2$ |
| DJ26 | 41 | 60 |
| DJ53 | 27 | 90 |
| Bui1 | 45 | 86 |
| TC3 | 62 | 100 |

As can be seen in Table 5 above, a portion of each family survived when fed the DvSnf7 dsRNA. A Chi-square test indicated percent survival in all four families was not significantly different from the fifty percent expected survival if the field collected male heterozygous for the RNAi resistant trait. An analysis using a Bayesian approach showed the DvSnf7 resistant allele frequency in the field collected population is 0.0214 with a lower confidence interval of 0.0139 and an upper confidence interval of 0.0315.

Example 5

DvSnf7 dsRNA Resistant Western Corn Rootworms are Unable to Uptake dsRNA and are Cross Resistant to Other dsRNA This example describes the allele conferring resistance to the DvSnf7 dsRNA results in a lack of uptake of dsRNA.

Adults from both the DvSnf7 dsRNA resistant and susceptible colonies were injected with twenty-five nanograms of DvSnf7 dsRNA or a chimeric RNA comprising GFP operably linked to the DvSnf7 dsRNA (GFP/dsRNA). All susceptible adults (100%) died after injection. Mortality of the resistant adults remained below fifteen percent. Adults from both colonies injected with the DvSnf7 were analyzed for the DvSnf7 transcript. The susceptible adults showed a 12.54-fold reduction in DvSnf7 transcript compared to the susceptible adults injected with the GFP/dsRNA. The resistant adults showed a 1.53-fold reduction in DvSnf7 transcript compared to the susceptible adults injected with the GFP/dsRNA.

To better understand the lack of suppression of the DvSnf7 transcript in the resistant colony, small RNA (sRNA) sequencing was performed on a subset of F6 generation resistant and susceptible larvae that were exposed to corn roots expressing the DvSnf7 dsRNA. These were the same individuals assayed using real time PCR in Example 2 above. The sequenced sRNA's identified from the carcass and gut tissues of the susceptible larvae mapped to the two hundred and forty base pair sequence of the DvSnf7 dsRNA sequence that was expressed in the transgenic corn as well as corn endogenous RNAi's. The sequenced sRNA's identified from the carcass and gut tissues of a subset of the resistant larvae did not map to the two hundred and forty base pair sequence of the DvSnf7 dsRNA sequence that was expressed in the transgenic corn nor corn endogenous RNAi's. To further determine if the dsRNA was effectively taken up by the larval midgut cells of the resistant and susceptible colonies, the two hundred and forty base pair DvSnf7 dsRNA was labeled with Cy3 dye using the Silencer siRNA labeling kit—Cy™3 (Ambion, Ausin, Tex.) to allow microscopic examination of the cells. The Cy3 labeled DvSnf7 dsRNA was observed to localize in the gut cells of the susceptible larvae, but not in the resistant larvae gut cells.

Resistant larvae were also evaluated for cross resistance to another dsRNA toxic to the susceptible larvae. Both resistant and susceptible larvae were exposed to an artificial diet overlaid with either a vATPase dsRNA, water, or a GFP vATPase dsRNA. The susceptible larvae showed a five-fold reduction in the transcript levels of the vATPase gene when exposed to the vATPase dsRNA when compared to exposure to water or the GFP vATPase dsRNA. The resistant larvae showed no suppression of the vATPase dsRNA when compared to exposure to water or the GFP vATPase dsRNA suggesting the resistant larvae are cross resistant to the vATPase dsRNA.

Example 6

The DvSnf7 dsRNA-Resistance Locus is Located on Linkage Group 4

This example describes the identification of the DvSnf7 dsRNA-resistance locus on linkage group 4.

To determine the location of potential DvSnf7 dsRNA resistance gene(s), reciprocal single parent crosses were made between WCR resistant and susceptible beetles. Two identical groups of F2 individuals arising from this cross were allowed to feed on two different maize plants. One group was allowed to feed upon maize plants expressing a dsRNA targeting for suppression the WCR essential gene DvSnf7 (MON87411 Event plants) and another group was allowed to feed upon a control plant lacking the dsRNA gene expression genotype. Survivors from each of five families (A1, A2, A5, B6, and B9) were genotyped using the WCR SNP genotyping platform (Flagel L E, Swarup S, Chen M, Bauer C, Wanjugi H, et al. (2015) *Genetic markers for western corn rootworm resistance to Bt toxin. G3: Genes| Genomes| Genetics* 5: 399-405). Chi-square tests were performed on genotype counts for the survivors and plotted along the genetic map. A single resistance locus was observed on the right end of linkage group 4 (LG4) in all five mapping families. As observed in the phenotypic assay described in Example 3 above, the LG4 resistance locus is autosomal, and accordingly, is detected in crosses where either the maternal or paternal parent harbored the resistance allele.

What is claimed is:

1. A RNAi resistant race of a Coleopteran species that is insensitive to endogenous gene suppression when exposed to an effective amount of environmental RNA targeting one or more endogenous essential genes, wherein said effective amount of RNA causes stunting or mortality to a susceptible race of said *Coleopteran* species, wherein said *Coleopteran* species is selected from the group of insect genus consisting of a *Diabrotica* and a *Leptinotarsa*, and wherein said *Diabrotica* is further selected from the group consisting of a Northern Corn Rootworm, a Southern Corn Rootworm, a Western Corn Rootworm, a Mexican Corn Rootworm, a Brazilian Corn Rootworm, and a South American Corn Rootworm Complex, and said Leptinotarsa is further characterized as a Colorado Potato Beetle.

2. The RNAi resistant race of a *Coleopteran* species of claim 1, for use optionally:

a) in assessing frequency of the resistance allele in a field;

b) to map the resistance allele or alleles on the chromosome of said *Coleopteran* species; and c) to develop compositions and methods for mediating or overcoming the resistance mechanism.

3. The RNAi resistant race of a *Coleopteran* species of claim 1, wherein said race is insensitive to gene suppression when environmental RNA levels targeting an essential gene in said species is provided in the diet of said species from about 0.1 ng/$cm^2$ to about 1,000 ng/$cm^2$ of said diet.

* * * * *

SEQUENCE LISTING

<160> NUMBER OF SEQ ID NOS: 7

<210> SEQ ID NO 1
<211> LENGTH: 630
<212> TYPE: DNA
<213> ORGANISM: Artificial
<220> FEATURE:
<223> OTHER INFORMATION: A a nucleic acid sequence encoding the DvSnf7 dsRNA used to create an RNAi resistant Western Corn Rootworm colony

<400> SEQUENCE: 1
atccatgata tcgtgaacat catctacatt caaattctta tgagctttct taagggcatc    60

-continued

```
tgcagcattt tcatagaat ctaatacagc agtatttgtg ctagctcctt cgagggcttc      120
cctctgcatt tcaatagttg taagggttcc atctatttgt agttgggtct tttccaatcg     180
tttcttcttt ttgagggctt ggagtgcaac tcttttattt ttcgacgcat ttttctttgc     240
aagtactgcg atcgcgttaa cgctttatca cgataccttc taccacatat cactaacaac     300
atcaacactc atcactctcg acgacatcca ctcgatcact actctcacac gaccgattaa     360
ctcctcatcc acgcggccgc ctgcaggagc gcaaagaaaa atgcgtcgaa aaataaaaga     420
gttgcactcc aagccctcaa aaagaagaaa cgattggaaa agacccaact acaaatagat     480 ggaacccctta caactattga aatgcagagg gaagccctcg aaggagctag cacaaatact    540
gctgtattag attctatgaa aaatgctgca gatgccctta agaaagctca taagaatttg     600
aatgtagatg atgttcacga tatcatggat                                      630
```

<210> SEQ ID NO 2
<211> LENGTH: 19
<212> TYPE: DNA
<213> ORGANISM: Artificial
<220> FEATURE:
<223> OTHER INFORMATION: The DvSnf7 forward primer used to quantify the DvSnf7 expression product in transgenic corn expressing the DvSnf7 transgene.

<400> SEQUENCE: 2

```
ccgacgatct ggatgacga                                                   19
```

<210> SEQ ID NO 3
<211> LENGTH: 19
<212> TYPE: DNA
<213> ORGANISM: Artificial
<220> FEATURE:
<223> OTHER INFORMATION: The DvSnf7 reverse primer used to quantify the DvSnf7 expression product in transgenic corn expressing the DvSnf7 transgene.

<400> SEQUENCE: 3

```
ttacgaggcc caggcttcc                                                   19
```

<210> SEQ ID NO 4
<211> LENGTH: 20
<212> TYPE: DNA
<213> ORGANISM: Artificial
<220> FEATURE:
<223> OTHER INFORMATION: A forward primer for amplification of a corn endogenous Actin gene used as a standard for quantification.

<400> SEQUENCE: 4

```
ggtgggtgga gcatagtgac                                                  20
```

<210> SEQ ID NO 5
<211> LENGTH: 20
<212> TYPE: DNA
<213> ORGANISM: Artificial
<220> FEATURE:
<223> OTHER INFORMATION: A reverse primer for amplification of a corn endogenous Actin gene used as a standard for quantification.

<400> SEQUENCE: 5

```
ctggtccatt ttgccaattc                                                  20
```

<210> SEQ ID NO 6
<211> LENGTH: 20
<212> TYPE: DNA
<213> ORGANISM: Artificial

-continued

```
<220> FEATURE:
<223> OTHER INFORMATION: A forward primer for amplification of a corn
      endogenous Tubulin gene used as a standard for quantification.

<400> SEQUENCE: 6
ccaagagagc tttcgtccac                                              20

<210> SEQ ID NO 7
<211> LENGTH: 20
<212> TYPE: DNA
<213> ORGANISM: Artificial
<220> FEATURE:
<223> OTHER INFORMATION: A reverse primer for amplification of a corn
      endogenous Tubulin gene used as a standard for quantification.

<400> SEQUENCE: 7
ttcagctcct tcaccctcac                                              20
```